(12) United States Patent
Shin et al.

(10) Patent No.: US 11,741,610 B2
(45) Date of Patent: Aug. 29, 2023

(54) METHOD FOR HOSPITAL VISIT GUIDANCE FOR MEDICAL TREATMENT FOR ACTIVE THYROID EYE DISEASE, AND SYSTEM FOR PERFORMING SAME

(71) Applicant: THYROSCOPE INC., Ulsan (KR)

(72) Inventors: Kyubo Shin, Ulsan (KR); Jongchan Kim, Ulsan (KR); Jaemin Park, Busan (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 17/945,270

(22) Filed: Sep. 15, 2022

(65) Prior Publication Data

US 2023/0013792 A1    Jan. 19, 2023

Related U.S. Application Data

(63) Continuation of application No. PCT/KR2022/009452, filed on Jun. 30, 2022.

(30) Foreign Application Priority Data

Jun. 30, 2021 (KR) .................. 10-2021-0085542
Jun. 30, 2022 (KR) .................. 10-2022-0080423

(51) Int. Cl.
*G06T 7/00* (2017.01)
*G16H 50/20* (2018.01)

(52) U.S. Cl.
CPC .......... *G06T 7/0016* (2013.01); *G16H 50/20* (2018.01); *G06T 2207/20081* (2013.01); *G06T 2207/30041* (2013.01); *G06T 2207/30201* (2013.01)

(58) Field of Classification Search
CPC .................................................. G06T 7/0016
See application file for complete search history.

(56) References Cited

U.S. PATENT DOCUMENTS

| | | |
|---|---|---|
| 2019/0370959 A1 | 12/2019 | Krishna et al. |
| 2020/0297206 A1 | 9/2020 | Zakharov et al. |
| 2022/0142484 A1* | 5/2022 | DiMaio ............. G16H 50/20 |

FOREIGN PATENT DOCUMENTS

| | | |
|---|---|---|
| CN | 109543728 A | 3/2019 |
| CN | 110246158 A | 9/2019 |

(Continued)

OTHER PUBLICATIONS

A. Kur et al. "Cellular and physiological mechanisms underlying blood flow regulation in the retina and choroid in health and disease" Elsevier (Year: 2012).*

(Continued)

*Primary Examiner* — Oneal R Mistry
(74) *Attorney, Agent, or Firm* — Dinsmore & Sholh LLP; Yongsok Choi, Esq.

(57) ABSTRACT

According to the present application, provided is a computer-implemented method of predicting a clinical activity score for conjunctival hyperemia. The method described in the present application includes: training a conjunctival hyperemia prediction model using a training set; acquiring a first image include at least one eye of a subject and an outer region of an outline of the at least one eye; outputting, by the conjunctival hyperemia prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema; and generating a score for the conjunctival hyperemia based on the selected first predicted value for a conjunctival hyperemia.

20 Claims, 24 Drawing Sheets

(56) References Cited

FOREIGN PATENT DOCUMENTS

| | | |
|---|---|---|
| CN | 111839455 A | 10/2020 |
| JP | 2016032587 A | 3/2016 |
| JP | 2017503276 A | 1/2017 |
| JP | 2018099174 A | 6/2018 |
| KR | 1020080105723 A | 12/2008 |
| KR | 1020140089132 A | 7/2014 |
| KR | 1020140105313 A | 9/2014 |
| KR | 1020140108417 A | 9/2014 |
| KR | 1020150107565 A | 9/2015 |
| KR | 1020190082149 A | 7/2019 |
| KR | 102047237 B1 | 12/2019 |
| KR | 102058883 B1 | 12/2019 |
| KR | 1020200005060 A | 1/2020 |
| KR | 1020200077461 A | 6/2020 |
| KR | 1020200108993 A | 9/2020 |
| KR | 1020200133923 A | 12/2020 |
| KR | 1020210004695 A | 1/2021 |
| KR | 102223478 B1 | 3/2021 |
| KR | 1020210026597 A | 3/2021 |
| KR | 102347551 B1 | 1/2022 |
| KR | 102379061 B1 | 4/2022 |
| WO | 2020023959 A1 | 1/2020 |

OTHER PUBLICATIONS

B. Fondi et al. "Evaluation of flicker induced hyperemia in the retina and optic nerve head measured by Laser Speckle Flogrphy" PLOS one. Jun. 18, 2018 (Year: 2018).*
C. Burns et al. "Imaging the Retinal Vasculature" HHS Public Access, available in PMC Mar. 15, 2022. (Year: 2022).*
Severity Classification of Conjunctival Hyperaemia by Deep Neural Network Ensembles, Received Nov. 27, 2018; Accepted May 10, 2019; Published Jun. 2, 2019, Hindawi (Year: 2019).*
Notice of Allowance of KR 10-2022-0079770 dated Oct. 31, 2022.
International Search Report and Written Opinion of PCT/KR2022/009452 dated Oct. 13, 2022.
International Search Report and Written Opinion of PCT/KR2022/009259 dated Oct. 6, 2022.
International Search Report and Written Opinion of PCT/KR2022/009356 dated Oct. 6, 2022.
Office Action of KR 10-2022-0080423 dated Sep. 20, 2022.
Notice of Allowance of KR 10-2021-0085542 dated Dec. 22, 2021.
Office Action of KR 10-2021-0085542 dated Aug. 20, 2021.

* cited by examiner

FIG. 13A
FIG. 13B
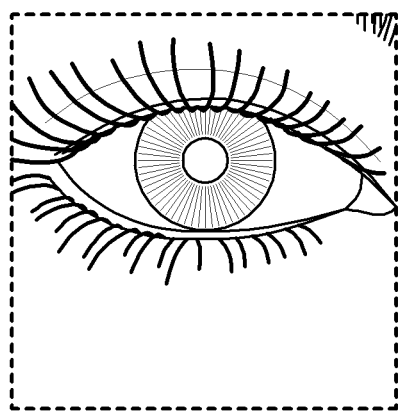
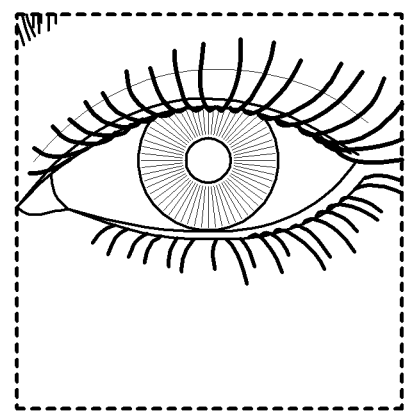

Center point

FIG. 17A
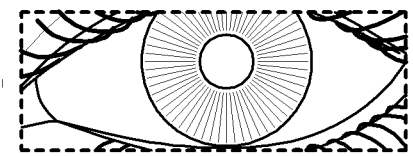 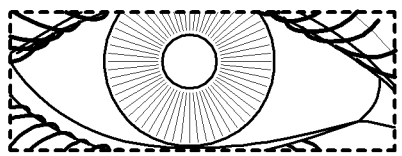
(FIRST LEFT EYE CROPPED IMAGE)　　(FIRST LATERAL INVERSION LEFT EYE CROPPED IMAGE)
FIG. 17B
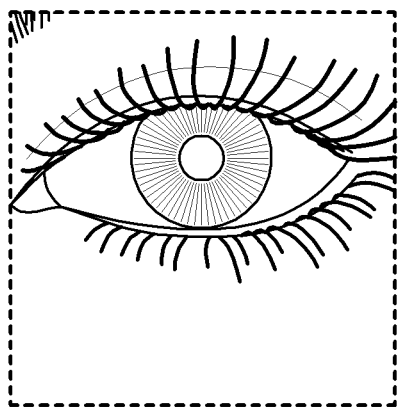 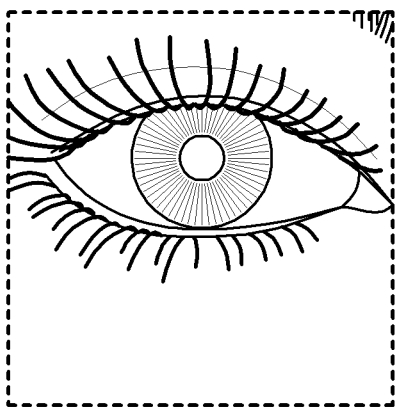
(SECOND LEFT EYE CROPPED IMAGE)　　(SECOND LATERAL INVERSION LEFT EYE CROPPED IMAGE)
FIG. 17C
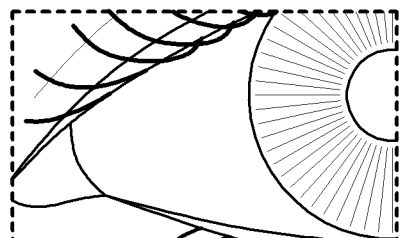 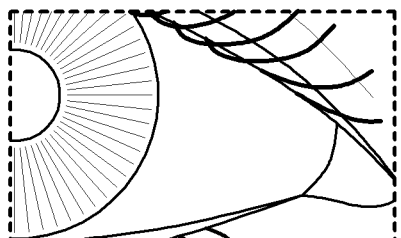
(THIRD LEFT EYE CROPPED IMAGE)　　(THIRD LATERAL INVERSION LEFT EYE CROPPED IMAGE)

FIG. 18A
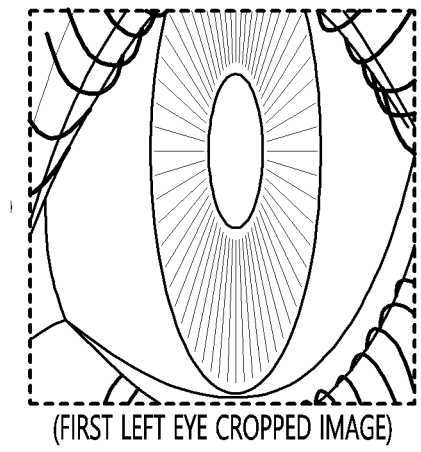
(FIRST LEFT EYE CROPPED IMAGE)
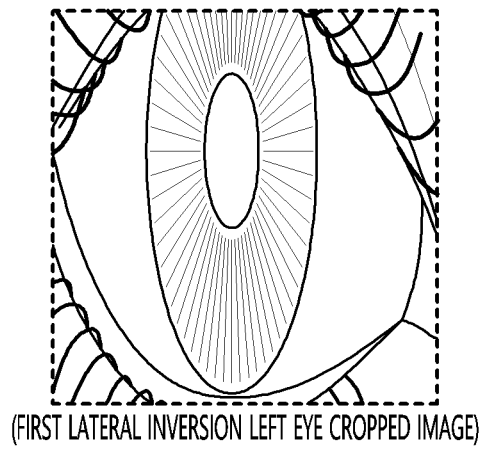
(FIRST LATERAL INVERSION LEFT EYE CROPPED IMAGE)
FIG. 18B
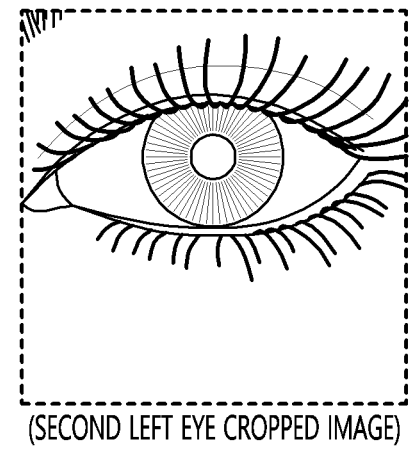
(SECOND LEFT EYE CROPPED IMAGE)
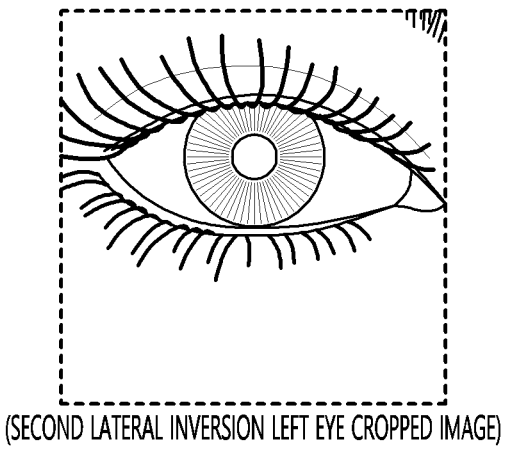
(SECOND LATERAL INVERSION LEFT EYE CROPPED IMAGE)
FIG. 18C
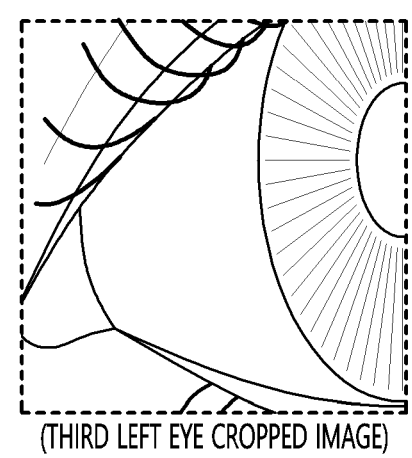
(THIRD LEFT EYE CROPPED IMAGE)
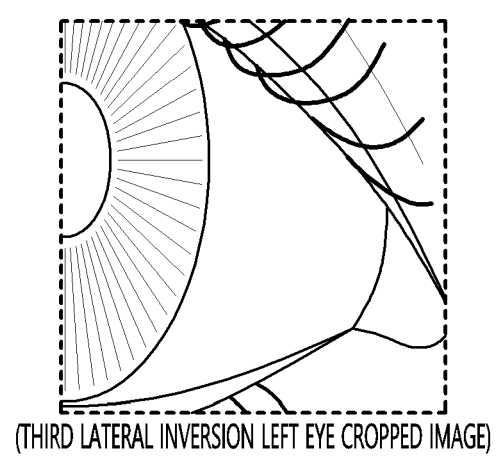
(THIRD LATERAL INVERSION LEFT EYE CROPPED IMAGE)

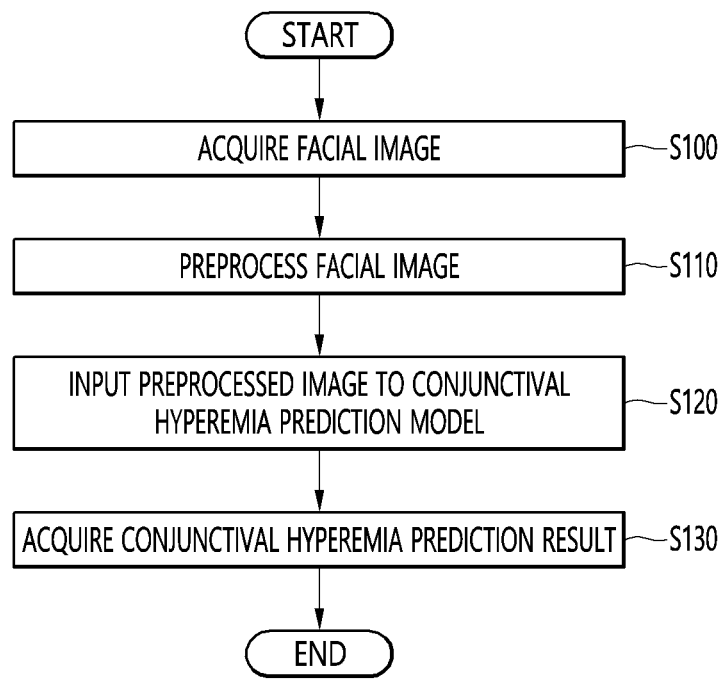

METHOD FOR HOSPITAL VISIT GUIDANCE FOR MEDICAL TREATMENT FOR ACTIVE THYROID EYE DISEASE, AND SYSTEM FOR PERFORMING SAME

CROSS-REFERENCE TO RELATED APPLICATIONS

This application is a continuation of International Application No. PCT/KR2022/009452 filed on Jun. 30, 2022, which claims priority to Korean Patent Application No. 10-2021-0085542 filed on Jun. 30, 2021 and Korean Patent Application No. 10-2022-0080423 filed on Jun. 30, 2022, the entire contents of which are herein incorporated by reference.

TECHNICAL FIELD

The present disclosure relates to a method for hospital visit guidance for medical treatment for active thyroid eye disease, and a system for performing the method.

BACKGROUND ART

An eye disease is a disease that occurs in the eyeball and surrounding parts. Many people in the world have been affected with eye diseases, and in severe cases, eye diseases cause great inconvenience in life, such as damage to eyesight, so it is necessary to monitor the occurrence or extent of the eye diseases.

In the meantime, an eye disease may be one of several complications caused by other diseases. For example, thyroid eye disease is a complication caused by thyroid dysfunction.

When thyroid eye disease becomes worse, the eyeball protrudes and cannot be treated without surgery. Therefore, early diagnosis of thyroid eye disease is very important for the treatment of thyroid eye disease. However, it is difficult to diagnose thyroid eye disease early because the disease does not show clear prognostic symptoms. In the medical community, efforts have been made to diagnose thyroid eye disease early through an evaluation method with the clinical activity score (CAS), which was proposed in 1989.

In determining the clinical activity score for thyroid eye disease, a total of seven items are considered, and the seven items are 1) spontaneous retrobulbar pain, 2) pain on an attempted upward or downward gaze, 3) redness of an eyelid, 4) redness of a conjunctiva, 5) swelling of an eyelid, 6) swelling of a conjunctiva, and 7) swelling of a lacrimal caruncle.

In order to determine a clinical activity score, it is essential that an individual visits a hospital or clinic in person and the doctor performs a medical examination through interview and observation with the naked eye. For example, spontaneous retrobulbar pain and pain on an attempted upward or downward gaze can be checked through interview by a doctor, and redness of an eyelid, redness of a conjunctiva, swelling of an eyelid, swelling of a conjunctiva, and swelling of a lacrimal caruncle can be checked by a doctor's observation with the naked eye. The doctor's medical examination with the naked eye and interview method for determining a clinical activity score require a hospital visit by a patient in person for a diagnosis of thyroid eye disease, as a precondition, so it is difficult to diagnose thyroid eye disease early.

Accordingly, it is desired to develop a method of enabling individuals to recognize a risk of eye disease more easily and quickly without a hospital visit in person so that continuous monitoring can be performed.

SUMMARY

Technical Problem

The disclosure in the present application is directed to providing a learning model used in predicting a clinical activity score for thyroid eye disease by using an image that is obtained with a digital camera that ordinary people can use rather than a professional medical diagnostic device.

In addition, the disclosure in the present application is directed to providing a method and a system for enabling ordinary people to continuously monitor a clinical activity score for thyroid eye disease without a doctor's help and a hospital visit in person.

Technical problems to be solved by the present application are not limited to the aforementioned technical problems and other technical problems which are not mentioned will be clearly understood by those skilled in the art from the present specification and the accompanying drawings.

Technical Solution

According to one aspect of the present application, A computer-implemented method is disclosed. The method comprising: training a conjunctival hyperemia prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, acquiring a first image include at least one eye of a subject and an outer region of an outline of the at least one eye, outputting, by the conjunctival hyperemia prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the conjunctival hyperemia among the five predicted values based on a predetermined setting, and generating a score for the conjunctival hyperemia based on the selected first predicted value for a conjunctival hyperemia.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the conjunctival hyperemia prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival hyperemia among the five predicted values based on a predetermined setting, and wherein the generating a score for the conjunctival hyperemia is generating a score for the conjunctival hyperemia considering the selected first predicted value for the conjunctival hyperemia and the selected second predicted value for the conjunctival hyperemia.

In some embodiments, wherein the generating the score for the conjunctival hyperemia comprises, assigning a predetermined value to the score: in response to determining that the first predicted value for the conjunctival hyperemia being greater than a threshold value, in response to determining that the second predicted value for the conjunctival hyperemia being greater than the threshold value, or in response to determining that the first and second predicted values for the conjunctival hyperemia being greater than the threshold value.

According to one aspect of the present application, A computer-implemented method is disclosed. The method comprising: training a conjunctival edema prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, acquiring a first image include at least one eye of a subject and an outer region of an outline of the at least one eye, outputting, by the conjunctival edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the conjunctival edema among the five predicted values based on a predetermined setting, and generating a score for the conjunctival edema based on the selected first predicted value for a conjunctival edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the conjunctival edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival edema among the five predicted values based on a predetermined setting, and wherein the generating a score for the conjunctival edema is generating a score for the conjunctival edema considering the selected first predicted value for the conjunctival edema and the selected second predicted value for the conjunctival edema.

In some embodiments, wherein the generating the score for the conjunctival edema comprises, assigning a predetermined value to the score: in response to determining that the first predicted value for the conjunctival edema being greater than a threshold value, in response to determining that the second predicted value for the conjunctival edema being greater than the threshold value, or in response to determining that the first and second predicted values for the conjunctival edema being greater than the threshold value.

According to one aspect of the present application, A computer-implemented method is disclosed. The method comprising: training a lacrimal edema prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the lacrimal edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the lacrimal edema among the five predicted values based on a predetermined setting, and generating a score for the lacrimal edema based on the selected first predicted value for a lacrimal edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the lacrimal edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the lacrimal edema among the five predicted values based on a predetermined setting, and wherein the generating a score for the lacrimal edema is generating a score for the lacrimal edema considering the selected first predicted value for the lacrimal edema and the selected second predicted value for the lacrimal edema.

In some embodiments, wherein the generating the score for the lacrimal edema comprises, assigning a predetermined value to the score: in response to determining that the first predicted value for the lacrimal edema being greater than a threshold value, in response to determining that the second predicted value for the lacrimal edema being greater than the threshold value, or in response to determining that the first and second predicted values for the lacrimal edema being greater than the threshold value.

According to one aspect of the present application, A computer-implemented method is disclosed. The method comprising: training an eyelid redness prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the eyelid redness prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid redness among the five predicted values based on a predetermined setting, and generating a score for the eyelid redness based on the selected first predicted value for the eyelid redness.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the eyelid redness model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid redness among the five predicted values based on a predetermined setting, and wherein the generating a score for the eyelid redness is generating a score for the eyelid redness considering the selected first predicted value for the eyelid redness and the selected second predicted value for the eyelid redness.

In some embodiments, wherein the generating the score for the eyelid redness comprises, assigning a predetermined value to the score: in response to determining that the first predicted value for the eyelid redness being greater than a threshold value, in response to determining that the second predicted value for the eyelid redness being greater than the threshold value, or in response to determining that the first and second predicted values for the eyelid redness being greater than the threshold value.

According to one aspect of the present application, A computer-implemented method is disclosed. The method comprising: training an eyelid edema prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the eyelid edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid edema among the five predicted values based on a predetermined setting, and generating a score for the eyelid edema based on the selected first predicted value for the eyelid edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the eyelid edema model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid edema among the five predicted values based on a predetermined setting, and wherein the generating a score for the eyelid edema is generating a score for the eyelid edema considering the selected first predicted value for the eyelid edema and the selected second predicted value for the eyelid edema.

In some embodiments, wherein the generating the score for the eyelid edema comprises, assigning a predetermined value to the score: in response to determining that the first predicted value for the eyelid edema being greater than a threshold value, in response to determining that the second predicted value for the eyelid edema being greater than the threshold value, or in response to determining that the first and second predicted values for the eyelid edema being greater than the threshold value.

Advantageous Effects

According to the disclosure in the present application, a clinical activity score for thyroid eye disease can be predicted using images obtained through a digital camera that ordinary people can use, rather than a professional medical diagnostic device.

DESCRIPTION OF DRAWINGS

FIGS. 13A and 13B are diagrams illustrating examples of second cropped images.

FIGS. 17A, 17B, and 17C are diagrams illustrating various examples of original images and laterally inverted images.

FIGS. 18A, 18B, and 18C are diagrams illustrating examples of resized images.

FIG. 19 is a flowchart illustrating a conjunctival hyperemia prediction method.

DETAILED DESCRIPTION

Figure 1:
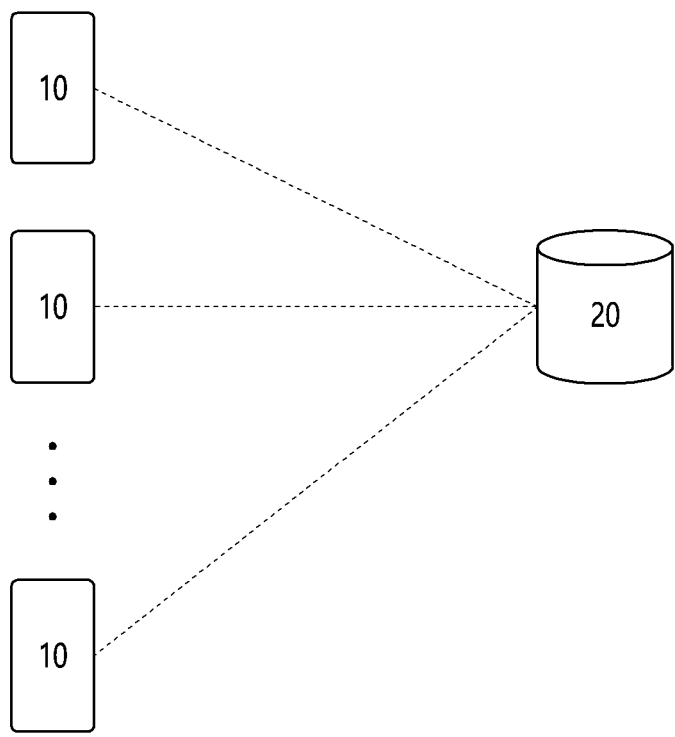
FIG. 1 is a diagram illustrating a system for predicting a clinical activity score for thyroid eye disease according to an embodiment described in the present application.

The above-described objectives, features, and advantages of the present application will be more apparent from the following detailed description with reference to the accompanying drawings. In addition, various modifications may be made to the present application, and various embodiments of the present application may be practiced. Therefore, specific embodiments will be described in detail below with reference to the accompanying drawings.

Throughout the specification, the same reference numerals denote the same elements in principle. In addition, elements having the same function within the same scope illustrated in the drawings of the embodiments are described using the same reference numerals, and a redundant description will be omitted.

A detailed description of a well-known function or configuration relating to the present application is omitted when determined as obfuscating the nature and gist of the present application. In addition, throughout the present specification, the terms first, second, and so on are used only to distinguish from one element to another.

In addition, the terms "module" and "part" that are used to name an element in the description below are used considering only the ease with which the present specification is written. The terms are not intended as having different special meanings or functions and thus may be used individually or interchangeably.

In the following embodiments, an expression used in the singular encompasses the expression of the plural, unless it has a clearly different meaning in the context.

In the following embodiments, it is to be understood that terms such as "including", "having", etc. are intended to indicate the existence of features or elements disclosed in the specification, and are not intended to preclude the possibility that one or more other features or elements may be added.

Sizes of elements in the drawings may be exaggerated or reduced for convenience of description. For example, any size and thickness of each element shown in the drawings are shown for convenience of description, and the present disclosure is not limited thereto.

In a case in which a particular embodiment is realized otherwise, a particular process may be performed out of the order described. For example, two processes described in succession may be performed substantially simultaneously, or may proceed in the order opposite to the order described.

In the following embodiments, when elements are referred to as being connected to each other, the elements are directly connected to each other or the elements are indirectly connected to each other with intervening elements therebetween. For example, in the present specification, when elements are referred to as being electrically connected to each other, the elements are directly electrically connected to each other or the elements are indirectly electrically connected with intervening elements therebetween.

According to one aspect of the present application, A computer-implemented method is disclosed. The method comprising: training a conjunctival hyperemia prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, acquiring a first image include at least one eye of a subject and an outer region of an outline of the at least one eye, outputting, by the conjunctival hyperemia prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the conjunctival hyperemia among the five predicted values based on a predetermined setting, and generating a score for the conjunctival hyperemia based on the selected first predicted value for a conjunctival hyperemia.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the conjunctival hyperemia prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival hyperemia among the five predicted values based on a predetermined setting, and wherein the generating a score for the conjunctival hyperemia is generating a score for the conjunctival hyperemia considering the selected first predicted value for the conjunctival hyperemia and the selected second predicted value for the conjunctival hyperemia.

In some embodiments, wherein the generating the score for the conjunctival hyperemia comprises, assigning a predetermined value to the score: in response to determining that the first predicted value for the conjunctival hyperemia being greater than a threshold value, in response to determining that the second predicted value for the conjunctival hyperemia being greater than the threshold value, or in response to determining that the first and second predicted values for the conjunctival hyperemia being greater than the threshold value.

According to one aspect of the present application, A computer-implemented method is disclosed. The method comprising: training a conjunctival edema prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, acquiring a first image include at least one eye of a subject and an outer region of an outline of the at least one eye, outputting, by the conjunctival edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the conjunctival edema among the five predicted values based on a predetermined setting, and generating a score for the conjunctival edema based on the selected first predicted value for a conjunctival edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the conjunctival edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival edema among the five predicted values based on a predetermined setting, and wherein the generating a score for the conjunctival edema is generating a score for the conjunctival edema considering the selected first predicted value for the conjunctival edema and the selected second predicted value for the conjunctival edema.

In some embodiments, wherein the generating the score for the conjunctival edema comprises, assigning a predetermined value to the score: in response to determining that the first predicted value for the conjunctival edema being greater than a threshold value, in response to determining that the second predicted value for the conjunctival edema being greater than the threshold value, or in response to determining that the first and second predicted values for the conjunctival edema being greater than the threshold value.

According to one aspect of the present application, A computer-implemented method is disclosed. The method comprising: training a lacrimal edema prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the lacrimal edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the lacrimal edema among the five predicted values based on a predetermined setting, and generating a score for the lacrimal edema based on the selected first predicted value for a lacrimal edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the lacrimal edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the lacrimal edema among the five predicted values based on a predetermined setting, and wherein the generating a score for the lacrimal edema is generating a score for the lacrimal edema considering the selected first predicted value for the lacrimal edema and the selected second predicted value for the lacrimal edema.

In some embodiments, wherein the generating the score for the lacrimal edema comprises, assigning a predetermined value to the score: in response to determining that the first predicted value for the lacrimal edema being greater than a threshold value, in response to determining that the second predicted value for the lacrimal edema being greater than the threshold value, or in response to determining that the first and second predicted values for the lacrimal edema being greater than the threshold value.

According to one aspect of the present application, A computer-implemented method is disclosed. The method comprising: training an eyelid redness prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the eyelid redness prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid redness among the five predicted values based on a predetermined setting, and generating a score for the eyelid redness based on the selected first predicted value for the eyelid redness.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the eyelid redness model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid redness among the five predicted values based on a predetermined setting, and wherein the generating a score for the eyelid redness is generating a score for the eyelid redness considering the selected first predicted value for the eyelid redness and the selected second predicted value for the eyelid redness.

In some embodiments, wherein the generating the score for the eyelid redness comprises, assigning a predetermined value to the score: in response to determining that the first predicted value for the eyelid redness being greater than a threshold value, in response to determining that the second predicted value for the eyelid redness being greater than the threshold value, or in response to determining that the first and second predicted values for the eyelid redness being greater than the threshold value.

According to one aspect of the present application, A computer-implemented method is disclosed. The method comprising: training an eyelid edema prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the eyelid edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid edema among the five predicted values based on a predetermined setting, and generating a score for the eyelid edema based on the selected first predicted value for the eyelid edema.

In some embodiments, wherein the first image is generated in relation to any one eye among both eyes, and wherein the generated predicted values are predicted values for the one eye.

In some embodiments, the method further comprising: acquiring a second image comprising other eye and an outer region of an outline of the other eye of the subject, outputting, by the eyelid edema model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid edema among the five predicted values based on a predetermined setting, and wherein the generating a score for the eyelid edema is generating a score for the eyelid edema considering the selected first predicted value for the eyelid edema and the selected second predicted value for the eyelid edema.

In some embodiments, wherein the generating the score for the eyelid edema comprises, assigning a predetermined value to the score: in response to determining that the first predicted value for the eyelid edema being greater than a threshold value, in response to determining that the second predicted value for the eyelid edema being greater than the threshold value, or in response to determining that the first and second predicted values for the eyelid edema being greater than the threshold value.

According to the present application, disclosed is a system for predicting a clinical activity score (CAS) for a user's thyroid eye disease.

1. Whole System

(1) Hardware Construction of System

FIG. 1 is a diagram illustrating a system for predicting a clinical activity score for thyroid eye disease according to an embodiment described in the present application.

Referring to FIG. 1, the system 1 includes a plurality of user terminals 10 and a server 20.

Hereinafter, the plurality of user terminals 10 and the server 20 will be described in detail.

(2) Functions of User Terminals

The plurality of user terminals 10 transmit information to the server 20 over various networks, and receive information from the server 20.

The plurality of user terminals 10 obtain images (hereinafter, referred to as eye images) of users' upper eyelids, lower eyelids, and eyeballs exposed to the outside by the upper eyelids and the lower eyelids. The plurality of user terminals 10 may perform necessary processing on the obtained eye images, or may transmit the obtained eye images or the processed eye images to the server 20.

The plurality of user terminals 10 may receive, from the server 20, prediction results about clinical activity scores processed by the server 20.

(3) Functions of Server

The server 20 transmits information to the plurality of user terminals 10 over various networks, and receive information from the plurality of user terminals 10.

The server 20 may receive the eye images from the plurality of user terminals 10. Herein, the server 20 may process the eye images. Alternatively, the server 20 may receive the processed eye images.

The server 20 may obtain, on the basis of the processed eye images, prediction results about clinical activity scores for users' thyroid eye diseases.

The server 20 may transmit the prediction results about the clinical activity scores to the plurality of user terminals 10.

(4) Software Construction of System

In order for the system 1 to operate, several software constructions are required.

To perform communication between the user terminals 10 and the server 20, terminal software needs to be installed on the plurality of user terminals 10, and server software needs to be installed on the server 20.

In order to perform pre-processing necessary for the eye images, various preprocessing algorithms may be used.

A plurality of prediction models for predicting clinical activity scores on the basis of the preprocessed eye images may be used.

The plurality of preprocessing algorithms may be run by the terminal software installed on the user terminals 10, or may be run by the software installed on the server 20. Alternatively, some of the plurality of preprocessing algorithms may be executed by the user terminals 10, and the others may be executed by the server 20.

The plurality of prediction models may be run by the software installed on the server 20. Alternatively, the plurality of prediction models may be run by the terminal software installed on the user terminals 10. Alternatively, some of the plurality of prediction models may be executed by the user terminals 10, and the others may be executed by the server 20.

(5) Elements of User Terminal

Figure 2:
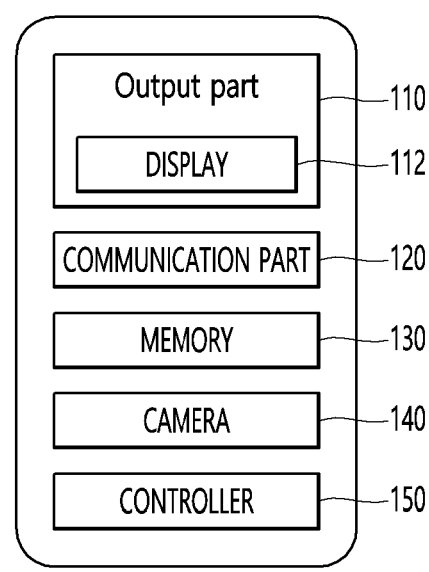
FIG. 2 is a block diagram illustrating a user terminal provided in the present application.

FIG. 2 is a block diagram illustrating a user terminal described in the present application.

Referring to FIG. 2, a user terminal 10 described in the present application includes an output part 110, a communication part 120, a memory 130, a camera 140, and a controller 150.

The output part 110 outputs various types of information according to control commands of the controller 150. According to an embodiment, the output part 110 may include a display 112 for outputting information visually to a user. Alternatively, although not shown in the drawings, a speaker for outputting information audibly to a user, and a vibration motor for outputting information tactually to a user may be included.

The communication part 120 may include a wireless communication module and/or a wired communication module. Herein, examples of the wireless communication module may include a Wi-Fi communication module, a cellular communication module, etc.

The memory 130 stores therein executable code readable by the controller 150, processed result values, necessary data, etc. Examples of the memory 130 may include a hard disk drive (HDD), a solid state disk (SSD), a silicon disk drive (SDD), ROM, RAM, etc. The memory 130 may store therein the above-described terminal software, and may store therein executable codes for realizing the above-described various preprocessing algorithms and/or learning models. Furthermore, the memory 130 may store therein an eye image obtained through the camera 140, the preprocessed eye images, etc.

The camera 140 is a digital camera, and may include an image sensor and an image processor. The image sensor is a device for converting an optical image into electrical signals, and may be provided as a chip in which multiple photodiodes are integrated. Examples of the image sensor may include a charge-coupled device (CCD), a complementary metal-oxide-semiconductor (CMOS), etc. In the meantime, the image processor may perform image processing on captured results, and may generate image information.

The controller 150 may include at least one processor. Herein, each of the processors may perform a predetermined operation by executing at least one instruction stored in the memory 130. Specifically, the controller 150 may process information according to the terminal software, the preprocessing algorithms, and/or the learning models running on the user terminal 10. In the meantime, the controller 150 controls the overall operation of the user terminal 10.

Although not shown in the drawings, the user terminal 10 may include a user input part. The user terminal 10 may receive, from a user, various types of information required for the operation of the user terminal 10 through the user input part.

(6) Elements of Server

Figure 3:
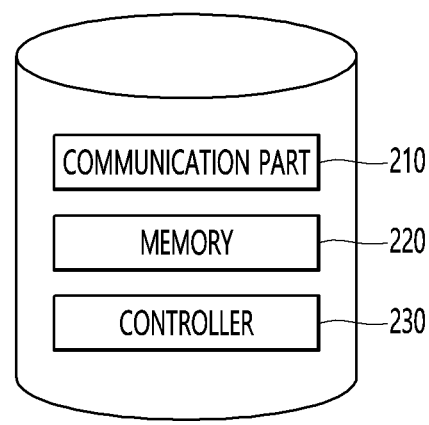
FIG. 3 is a block diagram illustrating a server described in the present application.

FIG. 3 is a block diagram illustrating a server described in the present application.

Referring to FIG. 3, the server 20 described in the present application includes a communication part 210, a memory 220, and a controller 230.

The communication part 210 may include a wireless communication module and/or a wired communication module. Herein, examples of the wireless communication module may include a Wi-Fi communication module, a cellular communication module, etc.

The memory 220 stores therein executable code readable by the controller 230, processed result values, necessary data, etc. Examples of the memory 220 may include a hard disk drive (HDD), a solid state disk (SSD), a silicon disk drive (SDD), ROM, RAM, etc. The memory 220 may store therein the above-described server software, and may store therein executable codes for realizing the above-described various preprocessing algorithms and/or learning models. Furthermore, the memory 220 may store therein an eye image received from the user terminal 10, the preprocessed eye images, etc.

The controller 230 may include at least one processor. Herein, each of the processors may perform a predetermined operation by executing at least one instruction stored in the memory 220. Specifically, the controller 230 may process information according to the server software, the preprocessing algorithms, and/or the learning models running on the server 20. In the meantime, the controller 230 controls the overall operation of the server 20.

Hereinafter, in order to more clearly and easily understand the technology described in the present application, an eye, an eyeball, and the tissues near the eyeball including an upper eyelid, a lower eyelid, and a lacrimal caruncle will be briefly described, and the terms related to an eye and the surroundings used in the present specification will be defined.

2. Construction of Eye and Definition of Terms (1) Eyeball and Surrounding Tissues FIG. 4 is a diagram illustrating an eye and the surrounding tissues that are exposed to the outside so that the eye and the surrounding tissues are captured by a camera when a picture of the face is taken using the camera.

Figure 4:
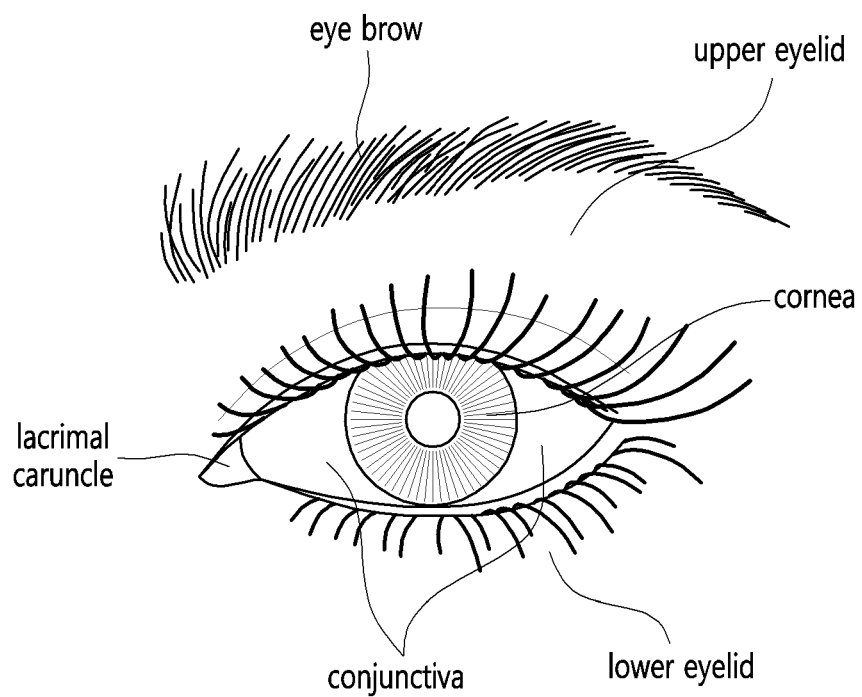
FIG. 4 is a diagram illustrating an eye and the surrounding tissues that are exposed to the outside so that the eye and the surrounding tissues are captured by a camera when a picture of the face is taken using the camera.

FIG. 4 shows the followings: eyelids (the upper eyelid and the lower eyelid); a lacrimal caruncle; a conjunctiva or the white of the eye partially exposed and partially covered by the upper eyelid, the lower eyelid, and the lacrimal caruncle; a cornea or iris; and an eyebrow.

In general, an eye or eyeball is larger than that shown in FIG. 4. However, an eyeball is protected from the outside by tissues, such as the upper eyelid, and the lower eyelid, and thus, only part of the eyeball is exposed to the outside even when the person has his or her eye open.

(2) Definition of Terms

Conjunctiva, White of Eye

Hereinafter, a conjunctiva generally corresponds to the position of the white of an eye, so the terms the conjunctiva and the white of the eye may be used interchangeably.

Cornea, Iris

Hereinafter, a cornea generally corresponds to the position of the iris of an eye, so the terms cornea and iris may be used interchangeably. In the meantime, in the present specification, the term 'iris' is used in a sense including a pupil region.

Eyelids

Eyelids are two, upper and lower folds of skin covering the front part of an eyeball. Eyelids are also called palpebrae. The eyelid above an eyeball is called the upper eyelid, and the eyelid below the eyeball is called the lower eyelid. The outer surface is skin and the inner surface is a conjunctiva, and therebetween, there are muscles moving the eyelids, and tarsal plates containing meibomian glands, which are sebaceous glands, thus maintaining the shape of the eyelids. The eyelids protect the eyeball, and simultaneously, make the eyeball clean with tears by blinking the eye or make the cornea shiny and transparent.

Eyebrow

An eyebrow refers to hairs grown in an arc along the bony ridge above an eye.

Eyelashes

Eyelashes refer to hairs about 10 mm in length on the edge of upper and lower eyelids.

Eyeball Exposed to Outside

Figure 5:
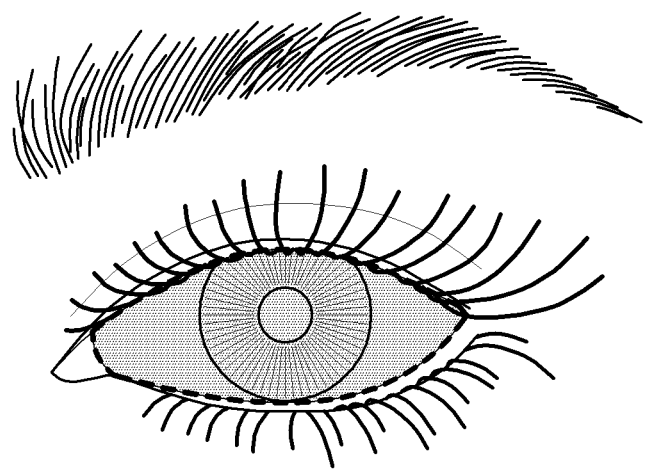
FIG. 5 is a diagram illustrating an eyeball exposed to the outside.

Hereinafter, "the eyeball exposed to the outside" means the part not covered by the upper eyelid, the lower eyelid, and the lacrimal caruncle, that is, the part exposed to the outside by the upper eyelid, the lower eyelid, and the lacrimal caruncle when a person has his or her eye open. For example, the inside of the dotted line shown in FIG. 5 is called "the eyeball exposed to the outside".

Outline of Eye

Hereinafter, "the outline of the eye" means the boundary between the eyeball exposed to the outside and the eyelids (the upper eyelid and the lower eyelid) when a person has his or her eye open. That is, the outline of the eyeball exposed to the outside is called "the outline of the eye". For example, the dotted line shown in FIG. 5 is called "the outline of the eye".

Cornea Exposed to Outside (Iris Exposed to Outside)

Figure 6:
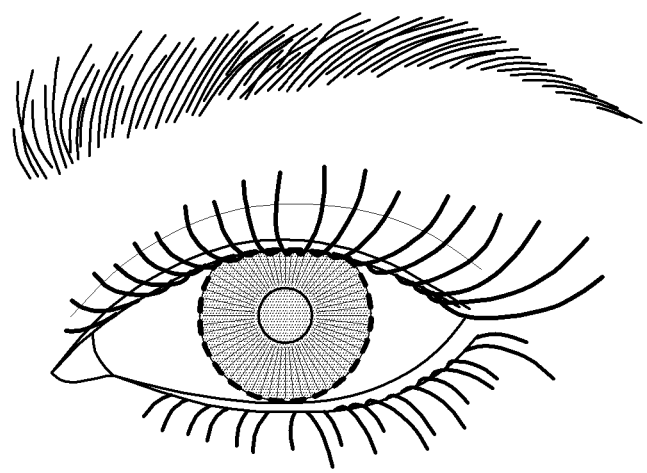
FIG. 6 is a diagram illustrating a cornea exposed to the outside.

Hereinafter, "the cornea exposed to the outside" means the cornea part not covered by the upper eyelid and the lower eyelid, that is, the cornea part exposed to the outside by the upper eyelid and the lower eyelid, when a person has his or her eye open. For example, the inside of the dotted line shown in FIG. 6 is called "the cornea exposed to the outside".

Conjunctiva Exposed to Outside (White of Eye Exposed to Outside)

Figure 7:
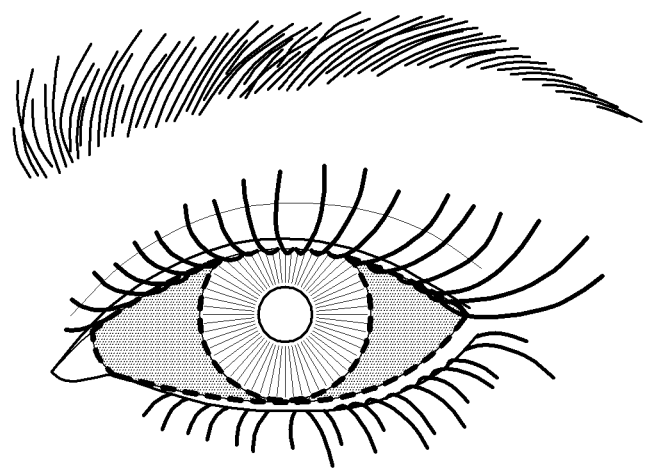
FIG. 7 is a diagram illustrating a conjunctiva exposed to the outside.

Hereinafter, "the conjunctiva exposed to the outside" means the conjunctiva part not covered by the upper eyelid, the lower eyelid, and the lacrimal caruncle, that is, the conjunctiva part exposed to the outside by the upper eyelid, the lower eyelid, and the lacrimal caruncle, when a person has his or her eye open. For example, the inside of the dotted line shown in FIG. 7 is called "the conjunctiva exposed to the outside".

Hereinafter, various image preprocessing algorithms for performing image preprocessing described in the present application will be described.

3. Image Preprocessing Algorithms (1) Necessity of Image Preprocessing

The present application is directed to providing a learning model for predicting a clinical activity score for thyroid eye disease by using an image obtained by a digital camera that ordinary people can use, rather than a professional medical diagnostic device.

To this end, in predicting a clinical activity score for thyroid eye disease, images that can be easily obtained by ordinary people for eyeballs and the tissues near the eyeballs need to be used. For example, an image analysis uses a digital image obtained by a digital camera or a camera built in a smartphone that can be easily used by ordinary people rather than a digital image obtained by a specialized medical device used in a medical institution.

Under this environment, a digital image obtained by a user is difficult to be standardized, and in order to more accurately and quickly recognize a digital image obtained by a user, various types of preprocessing of the obtained image are required.

Figure 8:
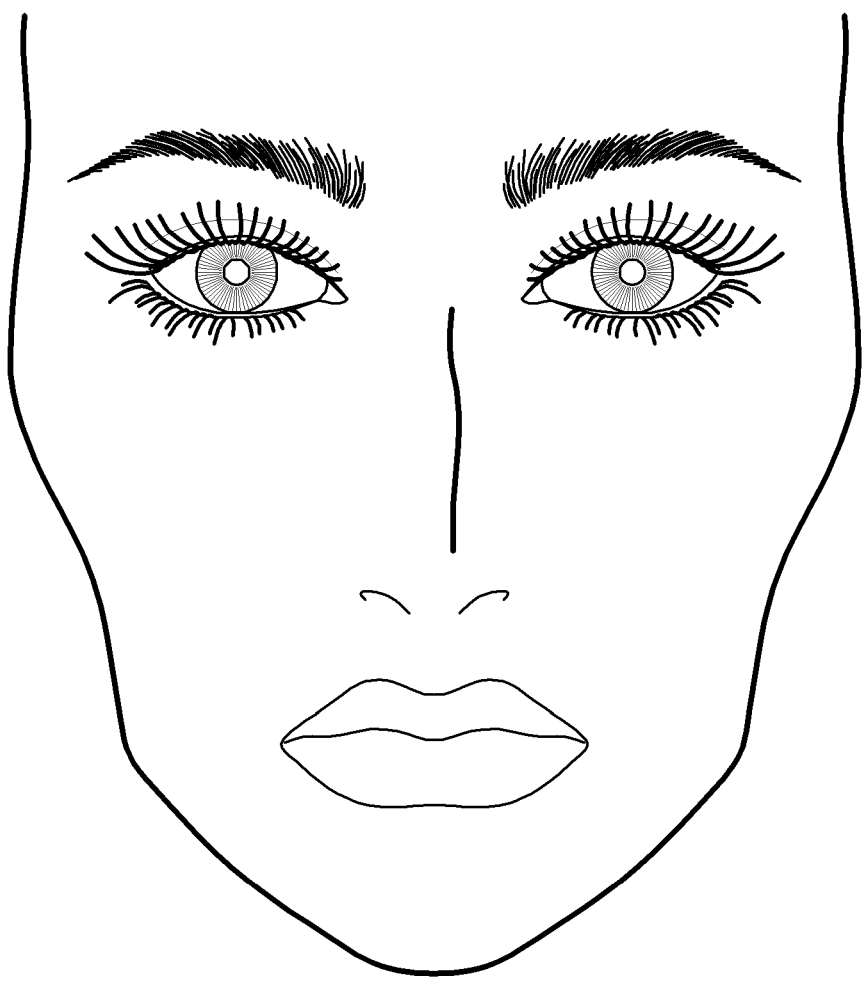
FIG. 8 is a diagram illustrating a facial image and a two-eye image.

In the meantime, the inventors of the present application built a system for predicting scores for five items related to thyroid eye disease by using a facial image as shown in FIG. 8, but it was found that the accuracy of prediction was low.

The inventors of the present application determined that the accuracy of prediction was low because the facial image included many regions unnecessary for an analysis, and determined that it is necessary to obtain a more elaborate cropped image.

(2) Necessity of Applying Different Cropping Methods

In the meantime, it has been described that five of the seven items for evaluating a clinical activity score for thyroid eye disease are the items evaluated according to a doctor's observation with the naked eye, of user's eyeballs and the surrounding regions. The five items evaluated according to a doctor's observation with the naked eye are as follows.

1) Conjunctival hyperemia (redness of conjunctiva),
2) Conjunctival edema (swelling of conjunctiva),
3) Lacrimal edema (swelling of lacrimal caruncle),
4) Redness of eyelid, and
5) Eyelid edema (swelling of eyelid).

Hereinafter, as will be described later, in order for evaluation, which is provided in the present application, of a clinical activity score for thyroid eye disease, it was determined that generating a total of three prediction models capable of performing prediction about a total of five symptoms may increase the accuracy of the prediction models, focusing on the point that a subject of observation with the naked eye is divided into three parts that are a "conjunctiva", a "lacrimal caruncle", and an "eyelid". That is, in training the three prediction models, it was determined that it would be more advantageous for the prediction models to have different cropping methods for images to be used as training data.

Hereinafter, described will be a cropping method more advantageous for an analysis of a "conjunctiva", a cropping method more advantageous for an analysis of a "lacrimal caruncle", and a cropping method more advantageous for an analysis of an "eyelid".

(3) First Cropping (Eyeball-Exposed-to-Outside Cropping)

Hereinafter, a cropping method more advantageous for a conjunctiva analysis will be described. This cropping method is called first cropping or eyeball-exposed-to-outside cropping. First cropping may be applied to both a right eye image and a left eye image, but a description will be given based on the case of obtaining a left eye cropped image for convenience.

Purpose of First Cropping

First cropping is to generate an image to be used as an input image of a model for predicting whether there is redness of a conjunctiva, and a model for predicting whether there is swelling of a conjunctiva among the prediction models to be described later. Second cropping is to generate an image in which information on the cornea exposed to the outside is maximized and information on the other regions is minimized.

Input Image

First cropping may be applied to a facial image or part of a facial image including both eyes.

Detection of Outline of Eye

According to an embodiment, a landmark detection algorithm may be used to detect an outline of an eye. For example, a facial landmark detection algorithm provided by dlib may be used to detect the pixels positioned at the outline of an eye.

Figure 9A:
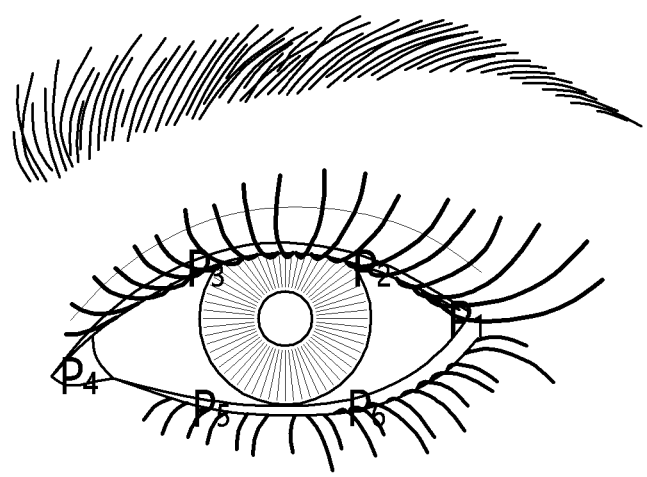
FIGS. 9A and 9B are diagrams illustrating a method of detecting an outline of an eye.

The numbers of pixels corresponding to the outline of an eye may vary depending on the types of landmark detection algorithms. However, according to the above-described facial landmark detection algorithm, six pixels may correspond to each of the outlines of both eyes and may be detected. One (for example, P4 shown in FIG. 9(a)) of the six pixels may correspond to the pixel determined as the leftmost part of the outline of an eye within an image. Another one (for example, P1 shown in FIG. 9(a)) of the six pixels may correspond to the pixel determined as the rightmost part of the outline of the eye within the image. Two other pixels (for example, P2 and P3 shown in FIG. 9(a)) of the six pixels may be the pixels corresponding to the boundary between the eyeball exposed to the outside and the upper eyelid within the image. The other two (for example, P5 and P6 shown in FIG. 9(a)) of the six pixels may be the pixels corresponding to the boundary between the eyeball exposed to the outside and the lower eyelid within the image.

In the present specification, detecting the outline of an eye may mean detecting all the pixels corresponding to the outline of the eye, or may mean detecting some of the pixels corresponding to the outline of the eye by using landmark detection, etc.

Hereinafter, a description will be given assuming the case of detecting six pixels corresponding to the outline of an eye.

Determination of First Cropped Region

Determining the detected pixels, a rectangle of the minimum size including all the six pixels is set. For example, the maximum value $X_{max}$ of the X coordinate values of the six pixels, the minimum value $X_{min}$ of the X coordinate values of the six pixels, the maximum value $Y_{max}$ of the Y coordinate values of the six pixels, and the minimum value $Y_{min}$ of the Y coordinate values of the six pixels are determined. On the basis of the determined $X_{max}$, $X_{min}$, $Y_{max}$, and $Y_{min}$, a quadrangle having the following four points as vertexes may be generated, and the region included inside the quadrangle may be determined as a first cropped region.

($X_{min}$, $Y_{max}$),
($X_{max}$, $Y_{max}$),
($X_{max}$, $Y_{min}$), and
($X_{min}$, $Y_{min}$)

Figure 10A:
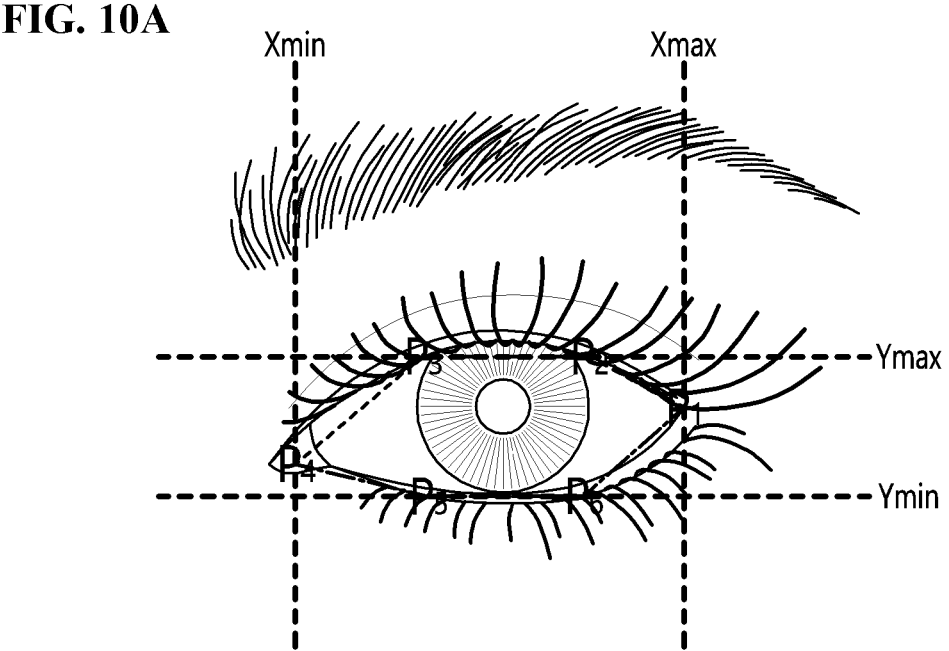
FIGS. 10A and 10B are diagrams illustrating a first cropped region.
Figure 10B:
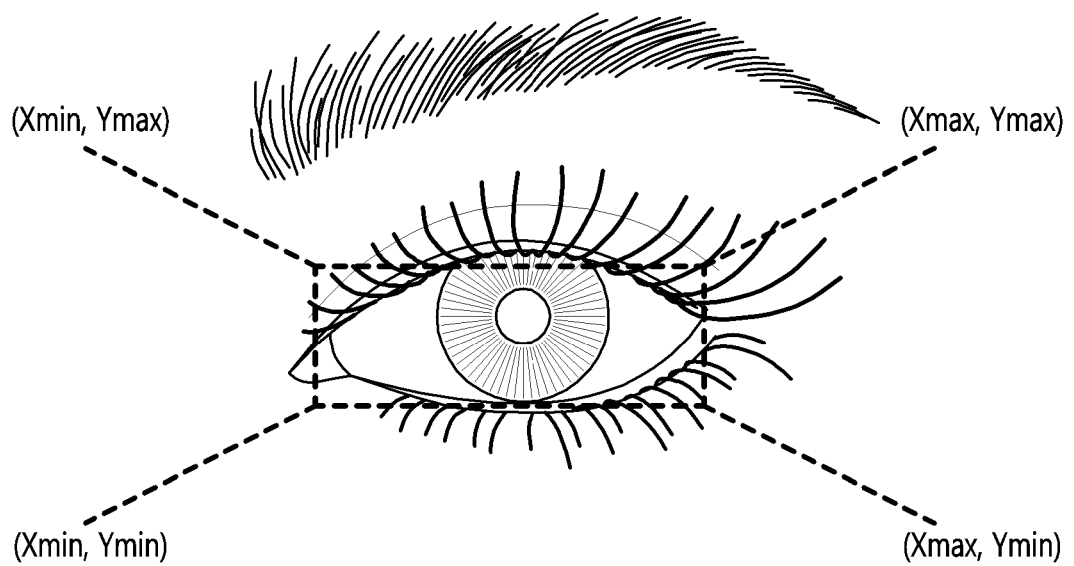

FIG. 10 is a diagram illustrating a first cropped region. In particular, FIG. 10(a) is a diagram illustrating determination of the maximum value $X_{max}$ of the X coordinate values of the above-described six pixels, the minimum value $X_{min}$ of the X coordinate values of the six pixels, the maximum value $Y_{max}$ of the Y coordinate values of the six pixels, and the minimum value $Y_{min}$ of the Y coordinate values of the six pixels. FIG. 10(b) is a diagram illustrating the first cropped region generated using the determined maximum value and minimum value of the X coordinates and the determined maximum value and minimum value of the Y coordinates.

As described above, the first cropped region may be determined in the same manner for the right eye.

Generation of First Cropped Images

Figure 11A:
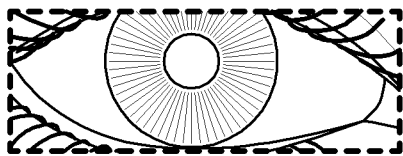
FIGS. 11A and 11B are diagrams illustrating examples of first cropped images.
Figure 11B:
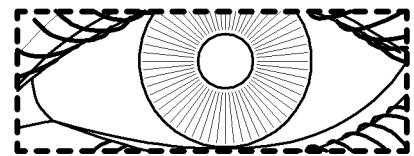

The first cropped regions are determined, and on the basis of the determined first cropped regions, as shown in FIG. 11 as an example, first cropped images may be generated from the facial image or part of the facial image including both eyes, by using the pixels included inside the first cropped regions. The first cropped images include a first right eye cropped image (FIG. 11(b)) generated for the right eye and a first left eye cropped image (FIG. 11(a)) generated for the left eye.

Hereinafter, the term "first cropped image" and the term "eyeball-exposed-to-outside cropped image" may be used interchangeably. The term "first right eye cropped image" and the term "right eyeball-exposed-to-outside cropped image" may be used interchangeably. The term "first left eye cropped image" and the term "left eyeball-exposed-to-outside cropped image" may be used interchangeably.

In addition, without specific mention hereinbelow, the term "first cropped image (or eyeball-exposed-to-outside cropped image)" may mean either a first right eye cropped image or a first left eye cropped image, or may mean both depending on the context.

A first cropped image means an image cropped in such a method that the ratio between the number of pixels corresponding to the eyeball exposed to the outside and the number of all pixels included in the cropped image is maximized. A cropped image generated in a method different from the above-described method is referred to as a first cropped image (eyeball-exposed-to-outside cropped image) if the cropped region is generated such that information on the eyeball exposed to the outside is contained as much as possible.

In the meantime, X coordinate values and Y coordinate values in the present application have different sizes and directions depending on a relative position with respect to a reference point, so the terms maximum value and minimum value should be understood in a relative sense, but not in an absolute sense. That is, as the position of the origin of the coordinate system is changed, the maximum value of the above-described X coordinate value may be the minimum value of the X coordinate value in the coordinate system of which the origin is changed, and the minimum value of the X coordinate value may be the maximum value of the X coordinate value in the coordinate system of which the origin is changed. This may be equally applied to the Y coordinate value.

(4) Second Cropping (Eyelid-Included Cropping)

Hereinafter, a cropping method more advantageous for eyelid analysis will be described. This cropping method is called second cropping or eyelid-included cropping. Second cropping may be applied to both a right eye image and a left eye image, but a description will be given based on the case of obtaining a left eye cropped image for convenience.

Purpose of Second Cropping

Second cropping is to generate an image to be used as an input image of a model for predicting whether there is redness of eyelids and a model for predicting whether there is swelling of eyelids among the prediction models to be described later. Second cropping is to include information on eyelids in the image. Herein, rather than cropping with only the pixels corresponding to eyelids, it may be better to generate a cropped image such that all the pixels included in the outline of the eye are included. This is because inference and determination are required for color values in order to predict whether there is eyelid redness, and the color values of the pixels corresponding to the iris and/or the white of the eye may be used.

Input Image

Second cropping may be applied to a facial image or part of a facial image including both eyes.

Detection of Outline of Eye, and Determination of Maximum Values and Minimum Values of X and Y Coordinates of Outline Pixels According to an embodiment, the eye outline detection method described in first cropping may be applied as it is. The outline pixels corresponding to the outermost part of the outline of the eye may be detected. Determining the detected pixels, the maximum value $X_{max}$ of the X coordinate values, the minimum value $X_{min}$ of the X coordinate values, the maximum value $Y_{max}$ of the Y coordinate values, and the minimum value $Y_{min}$ of the Y coordinate values may be determined. Hereinafter, for convenience of description, a quadrangle generated with the points determined using the above-described method as the vertexes is called a reference quadrangle. In the meantime, the horizontal length of the reference quadrangle is called a reference horizontal length or the horizontal length of the outline of the eye. The vertical length of the reference quadrangle is called a reference vertical length or the vertical length of the outline of the eye.

Cropped Region Determination

In order to determine a second cropped region having the shape of a quadrangle, the vertical length, the horizontal length, and the central point of the second cropped region are determined. When the coordinates of the vertexes of the second cropped region are (Xa,Ya), (Xa,Yb), (Xb, Ya), and (Xb, Yb) (herein, the value of Xa is lower than the value of Xb, and the value of Ya is lower than the value of Yb), the coordinates of the central point are determined to be ((Xa+Xb)/2, (Ya+Yb)/2) or ((Xa+(Xb−Xa)/2, Ya+(Yb+Ya)/2).

Vertical Length and Horizontal Length Determination #1

According to several embodiments, the vertical length of the second cropped region may be obtained by multiplying the reference vertical length by a predetermined number. The predetermined number may be 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0. In addition, the horizontal length of the second cropped region may be obtained by multiplying the reference horizontal length by a predetermined number. The predetermined number may be 1.1, 1.2, 1.3, 1.4, 1.5, 1.6, 1.7, 1.8, 1.9, 2.0, 2.1, 2.2, 2.3, 2.4, or 2.5. Herein, the predetermined number by which the reference vertical length is multiplied and the predetermined number by which the reference horizontal length is multiplied are determined independently of each other. Accordingly, the shape of the generated second cropped region may be a rectangle.

Vertical Length and Horizontal Length Determination #2

According to other several embodiments, the shape of the second cropped region may be a square. The length of one side of the second cropped region of the square may be determined on the basis of a value obtained by multiplying the reference vertical length by a predetermined number and a value obtained by multiplying the reference horizontal length by a predetermined number. For example, the greater value of the value obtained by multiplying the reference vertical length by the predetermined number and the value obtained by multiplying the reference horizontal length by the predetermined number may be determined as the length of one side. Herein, the predetermined number by which the reference vertical length is multiplied and the predetermined number by which the reference horizontal length is multiplied are determined independently of each other.

Determination of Position of Central Point

The position of the central point of the second cropped region may be different from the position of the central point of the reference quadrangle. The reason why the position of the central point of the reference quadrangle and the position of the central point of the second cropped region are determined to be different from each other is that the shapes of the upper eyelid and the lower eyelid are not symmetrical to each other and the shapes of the upper eyelid and the lower eyelid are generally not line-symmetrical with respect to the vertical line passing through the center of the reference quadrangle.

In general, the higher the y coordinate value of the central point of the second cropped region is than the y coordinate value of the central point of the reference quadrangle, the greater information on the eyebrow. The lower the y coordinate value of the central point of the second cropped region is than the y coordinate value of the central point of the reference quadrangle, the smaller the information on the eyebrow.

With respect to the left eye, in general, the higher the x coordinate value of the central point of the second cropped region is than the x coordinate value of the central point of the reference quadrangle, the smaller information on the region between the both eyes. The lower the x coordinate value of the central point of the second cropped region is than the x coordinate value of the central point of the reference quadrangle, the smaller information on the region between the eye and the temple.

In several embodiments of the present application, the y coordinate value of the central point of the second cropped region may be lower than the y coordinate value of the central point of the reference quadrangle.

In several embodiments of the present application, with respect to the left eye, the x coordinate value of the central point of the second cropped region may be higher than the x coordinate value of the central point of the reference quadrangle. However, with respect to the right eye, the x coordinate value of the central point of the second cropped region may be lower than the y coordinate value of the central point of the reference quadrangle.

However, the relationship between the position of the central point of the second cropped region and the position of the central point of the reference quadrangle is not necessarily the above-described relationship to achieve the objectives of the present application, and it is obvious to those skilled in the art that appropriate changes are allowed within a range capable of achieving the objectives of the present application.

FIG. 12 is a diagram illustrating examples of second cropped regions determined in various ways. FIG. 12(a) shows an example of a second cropped region in which the second cropped region is a rectangle and the central point of the second cropped region and the central point of the reference quadrangle match. FIG. 12(b) shows an example of a second cropped region in which the second cropped region is a rectangle and the central point of the second cropped region and the central point of the reference quadrangle do not match. FIG. 12(c) shows an example of a second cropped region in which the second cropped region is a square and the central point of the second cropped region and the central point of the reference quadrangle match. FIG. 12(d) shows an example of a second cropped region in which the second cropped region is a square and the central point of the second cropped region and the central point of the reference quadrangle do not match.

Figure 12A:
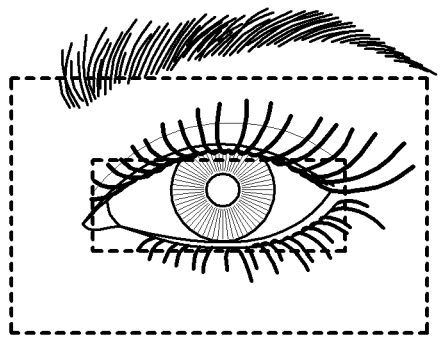
FIGS. 12A, 12B, 12C, and 12D are diagrams illustrating examples of second cropped regions determined in various ways.
Figure 12B:
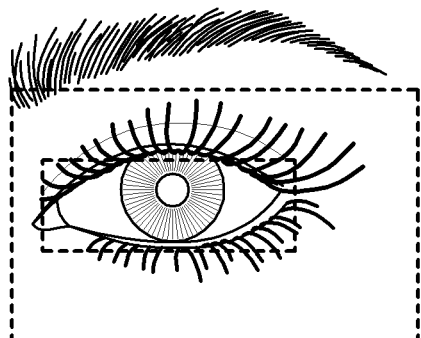
Figure 12C:
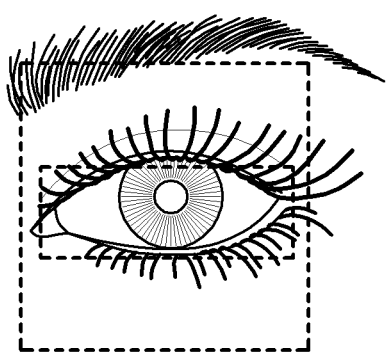
Figure 12D:
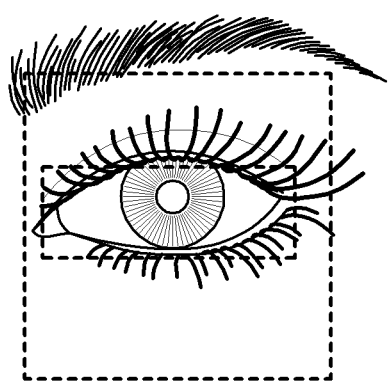

Hereinafter, for convenience, a description will be given based on the case in which a second cropped region is set as shown in FIG. 12(d).

Generation of Second Cropped Images

The second cropped regions are determined, and on the basis of the determined second cropped regions, as shown in FIG. 13, second cropped images may be generated from the facial image or part of the facial image including both eyes, by using the pixels included inside the second cropped regions. The second cropped images include a second right eye cropped image (FIG. 13(b)) generated for the right eye and a second left eye cropped image (FIG. 13(a)) generated for the left eye.

Hereinafter, the term "second cropped image" and the term "eyelid-included cropped image" may be used interchangeably. The term "second right eye cropped image" and the term "right eyelid-included cropped image" may be used interchangeably. The term "second left eye cropped image" and the term "left eyelid-included cropped image" may be used interchangeably.

In addition, without specific mention hereinbelow, the term "second cropped image (or eyelid-included cropped image)" may mean either a second right eye cropped image or a second left eye cropped image, or may mean both depending on the context.

A second cropped image means an image that is generated such that the image includes information on eyelids. A cropped image generated in a method different from the above-described method is referred to as a second cropped image (eyelid-included cropped image) if the boundary of the cropped region is determined such that the pixels corresponding to eyelids are additionally included.

(5) Third Cropping (Lacrimal Caruncle-Included Cropping)

Hereinafter, a cropping method more advantageous for a lacrimal caruncle analysis will be described. This cropping method is called third cropping or lacrimal caruncle-included cropping. Third cropping may be applied to both a right eye image and a left eye image, but a description will be given based on the case of obtaining a left eye cropped image for convenience.

Purpose of Third Cropping

Third cropping is to generate an image to be used as an input image of a model for predicting whether there is swelling of a lacrimal caruncle among the prediction models to be described later. Third cropping is to include information on a lacrimal caruncle in the image.

Input Image

Third cropping may be applied to a facial image or part of a facial image including both eyes.

Detection of Outline of Eye

According to an embodiment, the eye outline detection method in first cropping may be applied as it is. That is, six pixel values may be obtained through eye outline detection.

Cropped Region Determination

Hereinafter, a description will be given based on a left eye.

Figure 9B:
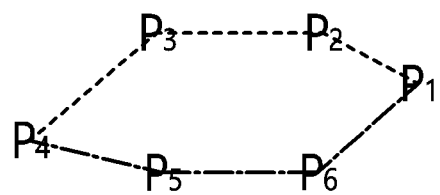
Figure 14A:
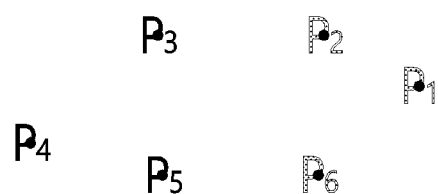
FIGS. 14A and 14B are diagrams illustrating a method of determining a third cropped region.

Among the six pixels, the following pixels are selected (FIG. 14(a)): the pixel ($P_4$ of FIG. 9, hereinafter, referred to as a first pixel) closest to the lacrimal caruncle; the pixel ($P_3$ of FIG. 9, hereinafter, referred to as a second pixel) closer to the lacrimal caruncle among the two pixels ($P_3$ and $P_2$ of FIG. 9) at the boundary between the upper eyelid or eyelashes on the upper eyelid side and the eyeball exposed to the outside; and the pixel ($P_5$ of FIG. 9, hereinafter, referred to as a third pixel) closer to the lacrimal caruncle among the two pixels ($P_5$ and $P_6$ of FIG. 9) at the boundary between the lower eyelid or eyelashes on the lower eyelid side and the eyeball exposed to the outside.

Figure 14B:
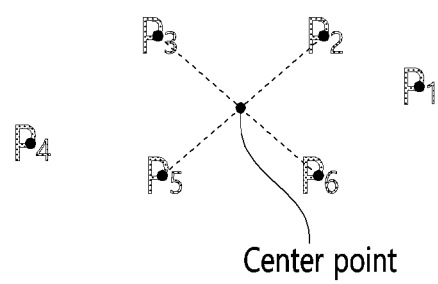

Next, the pixel (hereinafter, referred to as a fourth pixel) corresponding to the center point of the four pixels (P3, $P_2$, $P_5$, and $P_6$) at the boundary between the eyelashes and the eyeball exposed to the outside is determined (FIG. 14(b)).

Next, with respect to the above-described four pixels (the first to fourth pixels), the maximum value $X_{max}$ of the X coordinate values, the minimum value $X_{min}$ of the X coordinate values, the maximum value $Y_{max}$ of the Y coordinate values, and the minimum value $Y_{min}$ of the Y coordinate values may be determined.

On the basis of the determined $X_{max}$, $X_{min}$, $Y_{max}$, and $Y_{min}$, a quadrangle having the following four points as vertexes may be generated, and the region included inside the quadrangle may be determined as a third cropped region.

($X_{min}$, $Y_{max}$),
($X_{max}$, $Y_{max}$),
($X_{max}$, $Y_{min}$), and
($X_{min}$, $Y_{min}$)

Figure 15A:
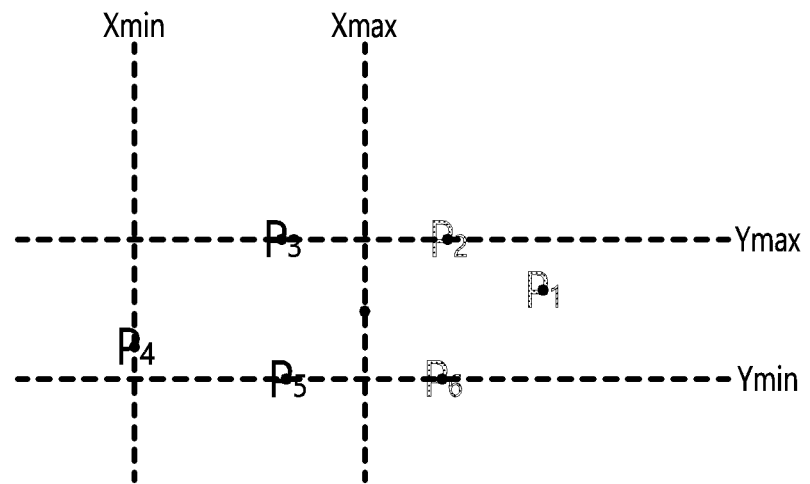
FIGS. 15A and 15B are diagrams illustrating an example of a third cropped region.
Figure 15B:
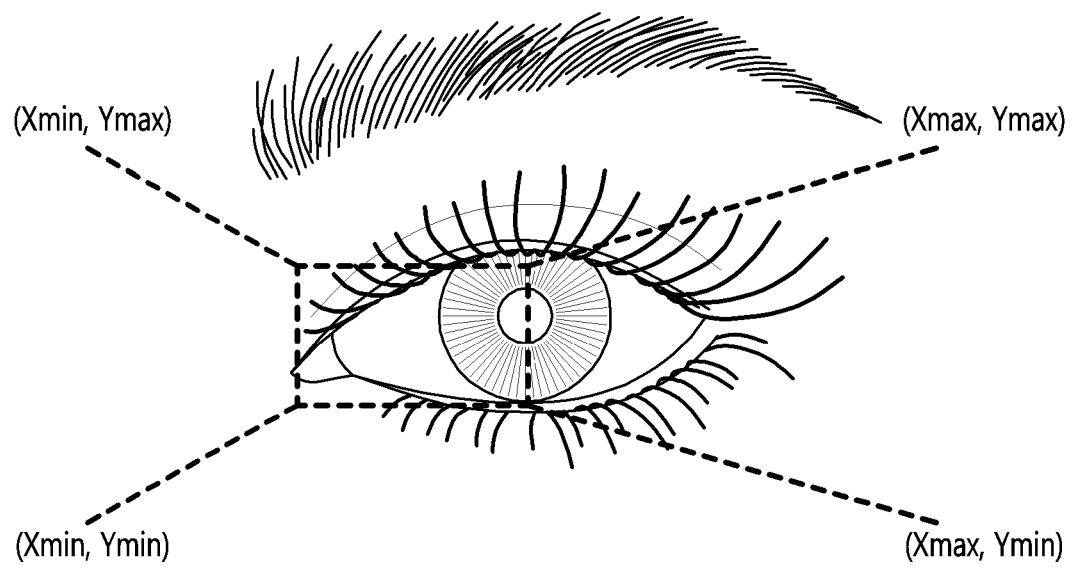

FIG. 15 is a diagram illustrating a third cropped region. In particular, FIG. 15(a) is a diagram illustrating determination of the maximum value $X_{max}$ of the X coordinate values of the above-described four pixels (the first to fourth pixels), the minimum value $X_{min}$ of the X coordinate values of the four pixels, the maximum value $Y_{max}$ of the Y coordinate values of the four pixels, and the minimum value $Y_{min}$ of the Y coordinate values of the four pixels. FIG. 15(b) is a diagram illustrating the third cropped region generated using the determined maximum value and minimum value of the X coordinates and the determined maximum value and minimum value of the Y coordinates.

As described above, the third cropped region may be determined in the same manner for the right eye.

Generation of Third Cropped Images

Figure 16A:
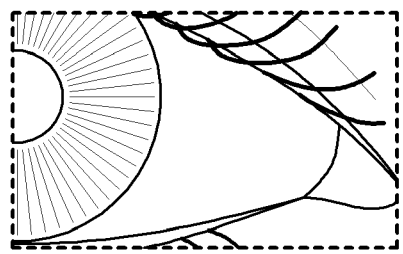
FIGS. 16A and 16B are diagrams illustrating examples of third cropped images.
Figure 16B:
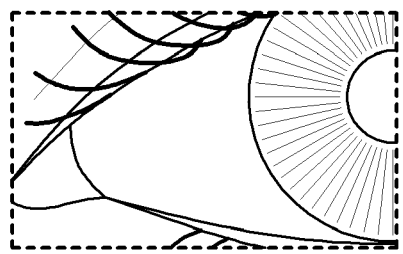

The third cropped regions are determined, and on the basis of the determined third cropped regions, as shown in FIG. 16, third cropped images may be generated from the facial image or part of the facial image including both eyes, by using the pixels included inside the third cropped regions. The third cropped images include a third right eye cropped image (FIG. 16(b)) generated for the right eye and a third left eye cropped image (FIG. 16(a)) generated for the left eye.

Hereinafter, the term "third cropped image" and the term "lacrimal caruncle-included cropped image" may be used interchangeably. The term "third right eye cropped image" and the term "right lacrimal caruncle-included cropped image" may be used interchangeably. The term "third left eye cropped image" and the term "left lacrimal caruncle-included cropped image" may be used interchangeably.

In addition, without specific mention hereinbelow, the term "third cropped image (or lacrimal caruncle-included cropped image)" may mean either a third right eye cropped image or a third left eye cropped image, or may include both depending on the context.

A third cropped image means an image that is generated such that the image includes information on a lacrimal caruncle. A cropped image generated in a method different from the above-described method is referred to as a third cropped image (lacrimal caruncle-included cropped image) if the boundary of the cropped region is determined such that the pixels corresponding to a lacrimal caruncle are included.

(6) Lateral Inversion

Necessity of Lateral Inversion

According to a method, which is provided in the present application, of predicting a clinical activity score for thyroid eye disease, cropped images of the left eye and the right eye are used instead of using a two-eye image.

In the meantime, the outline of an eye is asymmetric. For example, with respect to the right eye, the lacrimal caruncle is at the left end of the right eye, but the point at which the upper eyelid and the lower eyelid meet naturally is at the right end of the right eye.

Accordingly, for quicker learning and more accurate prediction, it is more effective to distinguish and use a prediction model trained with respect to a right eye and a prediction model trained with respect to a left eye.

However, when the left eye is turned over to be the right eye on the basis of the line of symmetry between the left eye and the right eye, the shape features of the right eye and the left eye are similar to each other.

Accordingly, according to the present application, either the right eye or the left eye is used without lateral inversion, the other eye is used with lateral inversion, so that only one prediction model can be used. Alternatively, when it is intended to train separate prediction models for the left eye and the right eye, training data sets may be doubled.

Lateral Inversion Method

Laterally inverting an image (converting the left and the right of the image) means that with a left and right reference line (X=a) vertically crossing the image to be inverted and dividing the image in half left and right, when a first pixel value corresponds to the pixel (a+Δ, Y) in the image and a second pixel value corresponds to the pixel (a−Δ, Y), the pixel value of (a+Δ, Y) is changed from the first pixel value to the second pixel value and the pixel value of (a−Δ, Y) is changed from the second pixel value to the first pixel value.

Lateral Inversion Target Image

Laterally inverting either the image of the left eye or the image of the right eye is sufficient. Which one of the left eye image and the right eye image is subjected to lateral inversion is determined according to which one of the left eye image and the right eye image is based when the prediction models, which will be described later, are trained.

FIG. 17 is a diagram illustrating various examples of original images and laterally inverted images. In particular, FIG. 17(a) illustrates a first cropped image and a laterally inverted image thereof. FIG. 17(b) illustrates a second cropped image and a laterally inverted image thereof. FIG. 17(c) illustrates a third cropped image and a laterally inverted image thereof.

Option of Lateral Inversion

However, as described above, lateral inversion is applied to unify a prediction model for the left eye and a prediction model for the right eye or to increase the amount of training data. Therefore, lateral inversion preprocessing may be omitted when necessary.

(8) Resizing

Necessity of Resizing

As described above, when an image is cropped with respect to the outline of the eye and the cropped image is used, sizes of eyes vary from person to person and cropped images vary in size from person to person.

In the meantime, when a left eye image and a right eye image are independently cropped and obtained, the left eye cropped image and the right eye cropped image of the same person are different from each other because of the difference in size between the left eye and the right eye.

For this reason, before an eye image is input to the prediction models, which will be described later, it is necessary to resize the eye image to standard sizes corresponding to the respective prediction models.

Standard Size for Each Prediction Model

The standard sizes corresponding to a first prediction model to a fifth prediction model, respectively, may be different from each other.

The standard sizes corresponding to the prediction models using a second cropped image as an input image may be the same.

The standard sizes corresponding to the prediction models using a third cropped image as an input image may be the same.

The standard size corresponding to the prediction models using a second cropped image as an input image may be different from the standard size corresponding to the prediction models using a third cropped image as an input image.

Alternatively, the standard sizes corresponding to the first prediction model to the fifth prediction model, respectively, may be the same.

FIG. 18 shows examples of resizing when the standard sizes of the first prediction model to the fifth prediction model are the same.

Resizing Method

The size of a resizing target image is adjusted to a standard size.

When the width or height of the resizing target image is greater than the width or height of the standard size, the width or height of the resizing target image may be decreased.

When the width or height of the resizing target image is less than the width or height of the standard size, the width or height of the resizing target image may be increased.

In resizing, the aspect ratio of the image before resizing may be different from the aspect ratio of the image after resizing.

4. Prediction Models (1) First Prediction Model

Purpose and Operation of First Prediction Model

The first prediction model is a model for predicting whether there is conjunctival hyperemia.

The first prediction model may receive an eye image as input data and may output a probability value that the conjunctiva captured in the input eye image is hyperemic. In particular, the first prediction model is a prediction model trained to predict whether there is conjunctival hyperemia, so the above-described first cropped image may be used for the first prediction model.

When the first prediction model includes a first left eye prediction model and a first right eye prediction model, the first left eye prediction model may receive a left eye image and output a probability value that the conjunctiva captured in the left eye image is hyperemic, and the first right eye prediction model may receive a right eye image and may output a probability value that the conjunctiva captured in the right eye image is hyperemic.

When the first prediction model is not dualized and is realized as one model, the first prediction model may receive either a right eye image or a left eye image to output a probability value that the conjunctiva captured in the input image is hyperemic, and may receive the other image to output a probability value that the conjunctiva captured in the input image is hyperemic.

The eye image may be an image preprocessed by the above-described preprocessing algorithms.

For example, the eye image may be an image on which preprocessing according to first cropping is performed.

As another example, the eye image may be an image on which preprocessing including first cropping and resizing is performed.

As still another example, the eye image may be an image on which preprocessing including first cropping, lateral inversion, and resizing is performed.

In the present specification, the first prediction model may be called a conjunctival hyperemia prediction model. However, the first prediction model described in the present application may output a result value for conjunctival edema prediction, a result value for lacrimal edema prediction, and result values for eyelid redness and eyelid edema prediction in addition to a result value for conjunctival hyperemia prediction.

Structure of Artificial Intelligence Model

To train the first prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

The first prediction model may employ ViT as the backbone architecture. The ViT model is a simple, non-hierarchical model with a single-scale feature map, and is a model proven to be effective for visual recognition.

The ViT is composed of linear embedding, a transformer encoder, and a classifier, and when an input image is input to the model, the input image may be divided into a plurality of input patches. The input patches resulting from division are supplied to the encoder and provided to the classifier, so that multiple labels are predicted.

In the present application, the artificial intelligence model may have five output nodes.

Preparation of Training Data Sets

To train the first prediction model, a plurality of training data sets may be prepared.

A training data set includes an eye image and a plurality of evaluated values corresponding thereto. The eye image is the above-described first cropped image, and the plurality of evaluated values include the following five evaluated values corresponding to the eye image: an evaluated value for conjunctival hyperemia, an evaluated value for conjunctival edema, an evaluated value for lacrimal edema, an evaluated value for eyelid redness, and an evaluated value for eyelid edema.

That is, in order to train the first prediction model for analyzing conjunctival hyperemia, a training data set including a first cropped image and only an evaluated value for conjunctival hyperemia corresponding thereto may be used, but in the present application, a first cropped image and all the above-described five types of evaluated values are used to train the first prediction model.

Accordingly, the first prediction model described in the present application is trained to consider symptoms of conjunctival edema, lacrimal edema, eyelid redness, and eyelid edema in analyzing conjunctival hyperemia, so that it is determined that conjunctival hyperemia is predicted more accurately.

Training of First Prediction Model

Using the plurality of training data sets prepared as described above, the eye images included in the prepared plurality of training data sets are input to the artificial intelligence model, and training is performed using the evaluated values corresponding to each of the input eye images and an output value output from the artificial intelligence model.

When the first prediction model includes the first left eye prediction model and the first right eye prediction model, the plurality of training data sets for training the first left eye prediction model may include: left eye images and evaluated values for conjunctival hyperemia, evaluated values for conjunctival edema, evaluated values for lacrimal edema, evaluated values for eyelid redness, and evaluated values for eyelid edema corresponding to the left eye images, and the plurality of training data sets for training the first right eye prediction model may include: right eye images and evaluated values for conjunctival hyperemia, evaluated values for conjunctival edema, evaluated values for lacrimal edema, evaluated values for eyelid redness, and evaluated values for eyelid edema corresponding to the right eye images. In the meantime, in order to increase the number of training data sets, the plurality of training data sets for training the first left eye prediction model may include right eye images on which lateral inversion is processed and five types of evaluated values corresponding to the right eye images, and the plurality of training data sets for training the first right eye prediction model may include left eye images on which lateral inversion is processed and five types of evaluated values corresponding to the left eye images.

When it is intended not to dualize the first prediction model, but to realize the first prediction model as one model, the plurality of training data sets may include right eye images and evaluated values for conjunctival hyperemia, evaluated values for conjunctival edema, evaluated values for lacrimal edema, evaluated values for eyelid redness, and evaluated values for eyelid edema corresponding to the right eye images, or may include left eye images on which lateral inversion is performed and evaluated values for conjunctival hyperemia, evaluated values for conjunctival edema, evaluated values for lacrimal edema, evaluated values for eyelid redness, and evaluated values for eyelid edema corresponding to the left eye images. Alternatively, the plurality of training data sets may include left eye images and five types of evaluated values corresponding to the left eye images, or may include right eye images on which lateral inversion is performed and five types of evaluated values corresponding to the right eye images.

In the meantime, in training the first prediction model, in order to predict whether there is conjunctival hyperemia without distinguishing between right eye images and left eye images, all right eye images, right eye images on which lateral inversion is performed, left eye images, and left eye images on which lateral inversion is performed are used as training data for training one model.

For example, when the first prediction model includes the first left eye prediction model and the first right eye prediction model, the plurality of training data sets for training the first left eye prediction model may include: left eye images and five types of evaluated values corresponding to the left eye images; and right eye images on which lateral inversion is performed and five types of evaluated values corresponding to the right eye images, and the plurality of training data sets for training the first right eye prediction model may include: right eye images and five types of evaluated values corresponding to the right eye images; and left eye images on which lateral inversion is performed and five types of evaluated values corresponding to the left eye images.

When it is intended not to dualize the first prediction model, but to realize the first prediction model as one model, the plurality of training data sets may include: right eye images and five types of evaluated values corresponding to the right eye images; right eye images on which lateral inversion is performed and five types of evaluated values corresponding to the right eye images; left eye images and five types of evaluated values corresponding to the left eye images; and left eye images on which lateral inversion is performed and five types of evaluated values corresponding to the left eye images.

(2) Second Prediction Model

Purpose and Operation of Second Prediction Model

The second prediction model is a model for predicting whether there is conjunctival edema.

The second prediction model may receive an eye image as input data and may output a probability value of the presence of conjunctival edema captured in the input eye image. In particular, the second prediction model is a prediction model trained to predict whether there is conjunctival edema, so the above-described first cropped image may be used for the second prediction models.

When the second prediction model includes a second left eye prediction model and a second right eye prediction model, the second left eye prediction model may receive a left eye image and output a probability value of the presence of conjunctival edema captured in the left eye image, and the second right eye prediction model may receive a right eye image and output a probability value of the presence of conjunctival edema captured in the right eye image.

When the second prediction model is not dualized and is realized as one model, the second prediction model may receive either a right eye image or a left eye image to output a probability value of the presence of conjunctival edema captured in the input image, and may receive the other image to output a probability value of the presence of conjunctival edema captured in the input image.

The eye image may be an image preprocessed by the above-described preprocessing algorithms.

For example, the eye image may be an image on which preprocessing according to first cropping is performed.

As another example, the eye image may be an image on which preprocessing including first cropping and resizing is performed.

As still another example, the eye image may be an image on which preprocessing including first cropping, lateral inversion, and resizing is performed.

In the present specification, the second prediction model may be called a conjunctival edema prediction model. However, the second prediction model described in the present application may output a result value for conjunctival hyperemia prediction, a result value for lacrimal edema prediction, and result values for eyelid redness and eyelid edema prediction in addition to a result value for conjunctival edema prediction.

Structure of Artificial Intelligence Model

To train the second prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

In the present application, the artificial intelligence model may have five output nodes.

A description of the artificial intelligence model for training the second prediction model is the same as or very similar to that of training the first prediction model described above, so a detailed description will be omitted here.

Preparation of Training Data Sets

To train the second prediction model, a plurality of training data sets may be prepared.

A training data set includes an eye image and a plurality of evaluated values corresponding thereto. The eye image is the above-described first cropped image, and the plurality of evaluated values include the following five evaluated values corresponding to the eye image: an evaluated value for conjunctival hyperemia, an evaluated value for conjunctival edema, an evaluated value for lacrimal edema, an evaluated value for eyelid redness, and an evaluated value for eyelid edema.

That is, in order to train the second prediction model for analyzing conjunctival edema, a training data set including a first cropped image and only an evaluated value for conjunctival edema corresponding thereto may be used, but in the present application, a first cropped image and all the above-described five types of evaluated values are used to train the second prediction model.

Accordingly, the second prediction model described in the present application is trained to consider symptoms of conjunctival hyperemia, lacrimal edema, eyelid redness, and eyelid edema in analyzing conjunctival edema, so that it is determined that conjunctival edema is predicted more accurately.

Training of Second Prediction Model

Using the plurality of training data sets prepared as described above, the eye images included in the prepared plurality of training data sets are input to the artificial intelligence model, and training is performed using the evaluated values corresponding to each of the input eye images and an output value output from the artificial intelligence model.

When the second prediction model includes the second left eye prediction model and the second right eye prediction model, the plurality of training data sets for training the second left eye prediction model may include: left eye images and evaluated values for conjunctival hyperemia, evaluated values for conjunctival edema, evaluated values for lacrimal edema, evaluated values for eyelid redness, and evaluated values for eyelid edema corresponding to the left eye images, and the plurality of training data sets for training the second right eye prediction model may include: right eye images and evaluated values for conjunctival hyperemia, evaluated values for conjunctival edema, evaluated values for lacrimal edema, evaluated values for eyelid redness, and evaluated values for eyelid edema corresponding to the right eye images. In the meantime, in order to increase the number of training data sets, the plurality of training data sets for training the second left eye prediction model may include right eye images on which lateral inversion is processed and five types of evaluated values corresponding to the right eye images, and the plurality of training data sets for training the second right eye prediction model may include left eye images on which lateral inversion is processed and five types of evaluated values corresponding to the left eye images.

When it is intended not to dualize the second prediction model, but to realize the second prediction model as one model, the plurality of training data sets may include right eye images and evaluated values for conjunctival hyperemia, evaluated values for conjunctival edema, evaluated values for lacrimal edema, evaluated values for eyelid redness, and evaluated values for eyelid edema corresponding to the right eye images, or may include left eye images on which lateral inversion is performed and evaluated values for conjunctival hyperemia, evaluated values for conjunctival edema, evaluated values for lacrimal edema, evaluated values for eyelid redness, and evaluated values for eyelid edema corresponding to the left eye images. Alternatively, the plurality of training data sets may include left eye images and five types of evaluated values corresponding to the left eye images, or may include right eye images on which lateral inversion is performed and five types of evaluated values corresponding to the right eye images.

In the meantime, in training the second prediction model, in order to predict whether there is conjunctival edema without distinguishing between right eye images and left eye images, all right eye images, right eye images on which lateral inversion is performed, left eye images, and left eye images on which lateral inversion is performed are used as training data for training one model.

For example, when the second prediction model includes the second left eye prediction model and the second right eye prediction model, the plurality of training data sets for training the second left eye prediction model may include: left eye images and five types of evaluated values corresponding to the left eye images; and right eye images on which lateral inversion is performed and five types of evaluated values corresponding to the right eye images, and the plurality of training data sets for training the second right eye prediction model may include: right eye images and five types of evaluated values corresponding to the right eye images; and left eye images on which lateral inversion is performed and five types of evaluated values corresponding to the left eye images.

When it is intended not to dualize the second prediction model, but to realize the second prediction model as one model, the plurality of training data sets may include: right eye images and five types of evaluated values corresponding to the right eye images; right eye images on which lateral inversion is performed and five types of evaluated values corresponding to the right eye images; left eye images and five types of evaluated values corresponding to the left eye images; and left eye images on which lateral inversion is performed and five types of evaluated values corresponding to the left eye images.

(3) Third Prediction Model

Purpose and Operation of Third Prediction Model

The third prediction model is a model for predicting whether there is lacrimal edema.

The third prediction model may receive an eye image as input data and may output a probability value of the presence of lacrimal edema captured in the input eye image. In particular, the third prediction model is a prediction model trained to predict whether there is lacrimal edema, so the above-described third cropped image may be used for the third prediction model.

When the third prediction model includes a third left eye prediction model and a third right eye prediction model, the third left eye prediction model may receive a left eye image and output a probability value of the presence of lacrimal edema captured in the left eye image, and the third right eye prediction model may receive a right eye image and output a probability value of the presence of lacrimal edema captured in the right eye image.

When the third prediction model is not dualized and is realized as one model, the third prediction model may receive either a right eye image or a left eye image to output a probability value of the presence of lacrimal edema captured in the input image, and may receive the other image to output a probability value of the presence of lacrimal edema captured in the input image.

The eye image may be an image preprocessed by the above-described preprocessing algorithms.

For example, the eye image may be an image on which preprocessing according to third cropping is performed.

As another example, the eye image may be an image on which preprocessing including third cropping and resizing is performed.

As still another example, the eye image may be an image on which preprocessing including third cropping, lateral inversion, and resizing is performed.

In the present specification, the third prediction model may be called a lacrimal edema prediction model. However, the third prediction model described in the present application may output a result value for conjunctival hyperemia prediction, a result value for conjunctival edema prediction, and result values for eyelid redness and eyelid edema prediction in addition to a result value for lacrimal edema prediction.

Structure of Artificial Intelligence Model

To train the third prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

In the present application, the artificial intelligence model may have five output nodes.

A description of the artificial intelligence model for training the third prediction model is the same as or very similar to that of training the first prediction model described above, so a detailed description will be omitted here.

Preparation of Training Data Sets

To train the third prediction model, a plurality of training data sets may be prepared.

A training data set includes an eye image and a plurality of evaluated values corresponding thereto. The eye image is the above-described third cropped image, and the plurality of evaluated values include the following five evaluated values corresponding to the eye image: an evaluated value for conjunctival hyperemia, an evaluated value for conjunctival edema, an evaluated value for lacrimal edema, an evaluated value for eyelid redness, and an evaluated value for eyelid edema.

That is, in order to train the third prediction model for analyzing lacrimal edema, a training data set including a third cropped image and only an evaluated value for lacrimal edema corresponding thereto may be used, but in the present application, a third cropped image and all the above-described five types of evaluated values are used to train the third prediction model.

Accordingly, the third prediction model described in the present application is trained to consider symptoms of conjunctival hyperemia, conjunctival edema, eyelid redness, and eyelid edema in analyzing lacrimal edema, so that it is determined that lacrimal edema is predicted more accurately.

Training of Third Prediction Model

Using the plurality of training data sets prepared as described above, the eye images included in the prepared plurality of training data sets are input to the artificial intelligence model, and training is performed using the evaluated values corresponding to each of the input eye images and an output value output from the artificial intelligence model.

When the third prediction model includes the third left eye prediction model and the third right eye prediction model, the plurality of training data sets for training the third left eye prediction model may include: left eye images and evaluated values for conjunctival hyperemia, evaluated values for conjunctival edema, evaluated values for lacrimal edema, evaluated values for eyelid redness, and evaluated values for eyelid edema corresponding to the left eye images, and the plurality of training data sets for training the third right eye prediction model may include: right eye images and evaluated values for conjunctival hyperemia, evaluated values for conjunctival edema, evaluated values for lacrimal edema, evaluated values for eyelid redness, and evaluated values for eyelid edema corresponding to the right eye images. In the meantime, in order to increase the number of training data sets, the plurality of training data sets for training the third left eye prediction model may include right eye images on which lateral inversion is processed and five types of evaluated values corresponding to the right eye images, and the plurality of training data sets for training the third right eye prediction model may include left eye images on which lateral inversion is processed and five types of evaluated values corresponding to the left eye images.

When it is intended not to dualize the third prediction model, but to realize the third prediction model as one model, the plurality of training data sets may include right eye images and evaluated values for conjunctival hyperemia, evaluated values for conjunctival edema, evaluated values for lacrimal edema, evaluated values for eyelid redness, and evaluated values for eyelid edema corresponding to the right eye images, or may include left eye images on which lateral inversion is performed and evaluated values for conjunctival hyperemia, evaluated values for conjunctival edema, evaluated values for lacrimal edema, evaluated values for eyelid redness, and evaluated values for eyelid edema corresponding to the left eye images. Alternatively, the plurality of training data sets may include left eye images and five types of evaluated values corresponding to the left eye images, or may include right eye images on which lateral inversion is performed and five types of evaluated values corresponding to the right eye images.

In the meantime, in training the third prediction model, in order to predict whether there is lacrimal edema without distinguishing between right eye images and left eye images, all right eye images, right eye images on which lateral inversion is performed, left eye images, and left eye images on which lateral inversion is performed are used as training data for training one model.

For example, when the third prediction model includes the third left eye prediction model and the third right eye prediction model, the plurality of training data sets for training the third left eye prediction model may include: left eye images and five types of evaluated values corresponding to the left eye images; and right eye images on which lateral inversion is performed and five types of evaluated values corresponding to the right eye images, and the plurality of training data sets for training the third right eye prediction model may include: right eye images and five types of evaluated values corresponding to the right eye images; and left eye images on which lateral inversion is performed and five types of evaluated values corresponding to the left eye images.

When it is intended not to dualize the third prediction model, but to realize the third prediction model as one model, the plurality of training data sets may include: right eye images and five types of evaluated values corresponding to the right eye images; right eye images on which lateral inversion is performed and five types of evaluated values corresponding to the right eye images; left eye images and five types of evaluated values corresponding to the left eye images; and left eye images on which lateral inversion is performed and five types of evaluated values corresponding to the left eye images.

(4) Fourth Prediction Model

Purpose and Operation of Fourth Prediction Model

The fourth prediction model is a model for predicting whether there is eyelid redness.

The fourth prediction model may receive an eye image as input data and may output a probability value of the presence of eyelid redness captured in the input eye image.

When the fourth prediction model includes a fourth left eye prediction model and a fourth right eye prediction model, the fourth left eye prediction model may receive a left eye image and output a probability value of the presence of eyelid redness captured in the left eye image, and the fourth right eye prediction model may receive a right eye image and output a probability value of the presence of eyelid redness captured in the right eye image.

When the fourth prediction model is not dualized and is realized as one model, the fourth prediction model may receive either a right eye image or a left eye image to output a probability value of the presence of eyelid redness captured in the input image, and may receive the other image to output a probability value of the presence of eyelid redness captured in the input image.

The eye image may be an image preprocessed by the above-described preprocessing algorithms.

For example, the eye image may be an image on which preprocessing according to second cropping is performed.

As another example, the eye image may be an image on which preprocessing including second cropping and resizing is performed.

As still another example, the eye image may be an image on which preprocessing including second cropping, lateral inversion, and resizing is performed.

In the present specification, the fourth prediction model may be called an eyelid redness prediction model. However, the fourth prediction model described in the present application may output a result value for conjunctival hyperemia prediction, a result value for conjunctival edema prediction, a result value for lacrimal edema prediction, and a result value for eyelid edema prediction in addition to a result value for eyelid redness prediction.

Structure of Artificial Intelligence Model

To train the fourth prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

In the present application, the artificial intelligence model may have five output nodes.

A description of the artificial intelligence model for training the fourth prediction model is the same as or very similar to that of training the first prediction model described above, so a detailed description will be omitted here.

Preparation of Training Data Sets

To train the fourth prediction model, a plurality of training data sets may be prepared.

A training data set includes an eye image and a plurality of evaluated values corresponding thereto. The eye image is the above-described second cropped image, and the plurality of evaluated values include the following five evaluated values corresponding to the eye image: an evaluated value for conjunctival hyperemia, an evaluated value for conjunctival edema, an evaluated value for lacrimal edema, an evaluated value for eyelid redness, and an evaluated value for eyelid edema.

That is, in order to train the fourth prediction model for analyzing eyelid redness, a training data set including a second cropped image and only an evaluated value for eyelid redness corresponding thereto may be used, but in the present application, a second cropped image and all the above-described five types of evaluated values may be used to train the fourth prediction model.

Accordingly, the fourth prediction model described in the present application is trained to consider symptoms of conjunctival hyperemia, conjunctival edema, lacrimal edema, and eyelid edema in analyzing eyelid redness, so that it is determined that eyelid redness is predicted more accurately.

Training of Fourth Prediction Model

Using the plurality of training data sets prepared as described above, the eye images included in the prepared plurality of training data sets are input to the artificial intelligence model, and training is performed using the evaluated values corresponding to each of the input eye images and an output value output from the artificial intelligence model.

When the fourth prediction model includes the fourth left eye prediction model and the fourth right eye prediction model, the plurality of training data sets for training the fourth left eye prediction model may include: left eye images and evaluated values for conjunctival hyperemia, evaluated values for conjunctival edema, evaluated values for lacrimal edema, evaluated values for eyelid redness, and evaluated values for eyelid edema corresponding to the left eye images, and the plurality of training data sets for training the fourth right eye prediction model may include: right eye images and evaluated values for conjunctival hyperemia, evaluated values for conjunctival edema, evaluated values for lacrimal edema, evaluated values for eyelid redness, and evaluated values for eyelid edema corresponding to the right eye images. In the meantime, in order to increase the number of training data sets, the plurality of training data sets for training the fourth left eye prediction model may include right eye images on which lateral inversion is processed and five types of evaluated values corresponding to the right eye images, and the plurality of training data sets for training the fourth right eye prediction model may include left eye images on which lateral inversion is processed and five types of evaluated values corresponding to the left eye images.

When it is intended not to dualize the fourth prediction model, but to realize the fourth prediction model as one model, the plurality of training data sets may include right eye images and evaluated values for conjunctival hyperemia, evaluated values for conjunctival edema, evaluated values for lacrimal edema, evaluated values for eyelid redness, and evaluated values for eyelid edema corresponding to the right eye images, or may include left eye images on which lateral inversion is performed and evaluated values for conjunctival hyperemia, evaluated values for conjunctival edema, evaluated values for lacrimal edema, evaluated values for eyelid redness, and evaluated values for eyelid edema corresponding to the left eye images. Alternatively, the plurality of training data sets may include left eye images and five types of evaluated values corresponding to the left eye images, or may include right eye images on which lateral inversion is performed and five types of evaluated values corresponding to the right eye images.

In the meantime, in training the fourth prediction model, in order to predict whether there is eyelid redness without distinguishing between right eye images and left eye images, all right eye images, right eye images on which lateral inversion is performed, left eye images, and left eye images on which lateral inversion is performed are used as training data for training one model.

For example, when the fourth prediction model includes the fourth left eye prediction model and the fourth right eye prediction model, the plurality of training data sets for training the fourth left eye prediction model may include: left eye images and five types of evaluated values corresponding to the left eye images; and right eye images on which lateral inversion is performed and five types of evaluated values corresponding to the right eye images, and the plurality of training data sets for training the fourth right eye prediction model may include: right eye images and five types of evaluated values corresponding to the right eye images; and left eye images on which lateral inversion is performed and five types of evaluated values corresponding to the left eye images.

When it is intended not to dualize the fourth prediction model, but to realize the fourth prediction model as one model, the plurality of training data sets may include: right eye images and five types of evaluated values corresponding to the right eye images; right eye images on which lateral inversion is performed and five types of evaluated values corresponding to the right eye images; left eye images and five types of evaluated values corresponding to the left eye images; and left eye images on which lateral inversion is performed and five types of evaluated values corresponding to the left eye images.

(5) Fifth Prediction Model

Purpose and Operation of Fifth Prediction Model

The fifth prediction model is a model for predicting whether there is eyelid edema.

The fifth prediction model may receive an eye image as input data and may output a probability value of the presence of eyelid edema captured in the input eye image.

When the fifth prediction model includes a fifth left eye prediction model and a fifth right eye prediction model, the fifth left eye prediction model may receive a left eye image and output a probability value of the presence of eyelid edema captured in the left eye image, and the fifth right eye prediction model may receive a right eye image and output a probability value of the presence of eyelid edema captured in the right eye image.

When the fifth prediction model is not dualized and is realized as one model, the fifth prediction model may receive either a right eye image or a left eye image to output a probability value of the presence of eyelid edema captured in the input image, and may receive the other image to output a probability value of the presence of eyelid edema captured in the input image.

The eye image may be an image preprocessed by the above-described preprocessing algorithms.

For example, the eye image may be an image on which preprocessing according to second cropping is performed.

As another example, the eye image may be an image on which preprocessing including second cropping and resizing is performed.

As still another example, the eye image may be an image on which preprocessing including second cropping, lateral inversion, and resizing is performed.

In the present specification, the fifth prediction model may be called an eyelid edema prediction model. However, the fifth prediction model described in the present application may output a result value for conjunctival hyperemia prediction, a result value for conjunctival edema prediction, a result value for lacrimal edema prediction, and a result value for eyelid redness prediction in addition to a result value for eyelid edema prediction.

Structure of Artificial Intelligence Model

To train the fifth prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

In the present application, the artificial intelligence model may have five output nodes.

A description of the artificial intelligence model for training the fifth prediction model is the same as or very similar to that of training the first prediction model described above, so a detailed description will be omitted here.

Preparation of Training Data Sets

To train the fifth prediction model, a plurality of training data sets may be prepared.

A training data set includes an eye image and a plurality of evaluated values corresponding thereto. The eye image is the above-described second cropped image, and the plurality of evaluated values include the following five evaluated values corresponding to the eye image: an evaluated value for conjunctival hyperemia, an evaluated value for conjunctival edema, an evaluated value for lacrimal edema, an evaluated value for eyelid redness, and an evaluated value for eyelid edema.

That is, in order to train the fifth prediction model for analyzing eyelid edema, a training data set including a second cropped image and only an evaluated value for eyelid edema corresponding thereto may be used, but in the present application, a second cropped image and all the above-described five types of evaluated values are used to train the fifth prediction model.

Accordingly, the fifth prediction model described in the present application is trained to consider symptoms of conjunctival hyperemia, conjunctival edema, lacrimal edema, and eyelid redness in analyzing eyelid edema, so that it is determined that eyelid edema is predicted more accurately.

Training of Fifth Prediction Model

Using the plurality of training data sets prepared as described above, the eye images included in the prepared plurality of training data sets are input to the artificial intelligence model, and training is performed using the evaluated values corresponding to each of the input eye images and an output value output from the artificial intelligence model.

When the fifth prediction model includes the fifth left eye prediction model and the fifth right eye prediction model, the plurality of training data sets for training the fifth left eye prediction model may include: left eye images and evaluated values for conjunctival hyperemia, evaluated values for conjunctival edema, evaluated values for lacrimal edema, evaluated values for eyelid redness, and evaluated values for eyelid edema corresponding to the left eye images, and the plurality of training data sets for training the fifth right eye prediction model may include: right eye images and evaluated values for conjunctival hyperemia, evaluated values for conjunctival edema, evaluated values for lacrimal edema, evaluated values for eyelid redness, and evaluated values for eyelid edema corresponding to the right eye images. In the meantime, in order to increase the number of training data sets, the plurality of training data sets for training the fifth left eye prediction model may include right eye images on which lateral inversion is processed and five types of evaluated values corresponding to the right eye images, and the plurality of training data sets for training the fifth right eye prediction model may include left eye images on which lateral inversion is processed and five types of evaluated values corresponding to the left eye images.

When it is intended not to dualize the fifth prediction model, but to realize the fifth prediction model as one model, the plurality of training data sets may include right eye images and evaluated values for conjunctival hyperemia, evaluated values for conjunctival edema, evaluated values for lacrimal edema, evaluated values for eyelid redness, and evaluated values for eyelid edema corresponding to the right eye images, or may include left eye images on which lateral inversion is performed and evaluated values for conjunctival hyperemia, evaluated values for conjunctival edema, evaluated values for lacrimal edema, evaluated values for eyelid redness, and evaluated values for eyelid edema corresponding to the left eye images. Alternatively, the plurality of training data sets may include left eye images and five types of evaluated values corresponding to the left eye images, or may include right eye images on which lateral inversion is performed and five types of evaluated values corresponding to the right eye images.

In the meantime, in training the fifth prediction model, in order to predict whether there is eyelid edema without distinguishing between right eye images and left eye images, all right eye images, right eye images on which lateral inversion is performed, left eye images, and left eye images on which lateral inversion is performed are used as training data for training one model.

For example, when the fifth prediction model includes the fifth left eye prediction model and the fifth right eye prediction model, the plurality of training data sets for training the fifth left eye prediction model may include: left eye images and five types of evaluated values corresponding to the left eye images; and right eye images on which lateral inversion is performed and five types of evaluated values corresponding to the right eye images, and the plurality of training data sets for training the fifth right eye prediction model may include: right eye images and five types of evaluated values corresponding to the right eye images; and left eye images on which lateral inversion is performed and five types of evaluated values corresponding to the left eye images.

When it is intended not to dualize the fifth prediction model, but to realize the fifth prediction model as one model, the plurality of training data sets may include: right eye images and five types of evaluated values corresponding to the right eye images; right eye images on which lateral inversion is performed and five types of evaluated values corresponding to the right eye images; left eye images and five types of evaluated values corresponding to the left eye images; and left eye images on which lateral inversion is performed and five types of evaluated values corresponding to the left eye images.

The training of the prediction models may be performed by an electronic device, and in particular, may be performed by the server 20 described above. Furthermore, the training of the prediction models by the electronic device or the server means a series of processes for enabling output values of the prediction models for input data to be values similar to output values labelled with the input data. To this end, the electronic device or the server 20 may use the differences between the output values of the prediction models and the labelled values to change a weight value of each of the nodes included in the prediction models. Herein, the electronic device or the server 20 may determine the amount of change in the weight value of each of the nodes by using various feedback functions.

Hereinafter, the following methods through the above-described system 1 will be described: a method of predicting each symptom related to a clinical activity score for thyroid eye disease by preprocessing an eye image and inputting the preprocessed eye image to the above-described prediction models; a method of predicting a clinical activity score on the basis of a prediction result for each symptom; and a method of monitoring a prediction result of a clinical activity score and giving guidance or recommendation according to the monitored result so that a user visits the hospital and has a medical examination.

5. Conjunctival Hyperemia Prediction Method

The conjunctival hyperemia prediction method described in the present application may be performed by the server 20.

FIG. 19 is a flowchart illustrating a conjunctival hyperemia prediction method.

Referring to FIG. 19, the server 20 acquires a facial image in step S100, preprocesses the acquired facial image in step S110, inputs the preprocessed image to the above-described first prediction model (conjunctival hyperemia prediction model) in step S120, and acquires an output value of the first prediction model in step S130.

Acquisition of Facial Image

The server 20 acquires a facial image in step S100. The server 20 may acquire the facial image from the user terminal 10.

Preprocessing of Facial Image

The server 20 may preprocess the acquired facial image in step S110. The server 20 may perform, on the acquired facial image, first cropping, lateral inversion, and resizing, which are described above.

Cropping Processing

The server 20 may crop the facial image or part of the facial image including both eyes. The server 20 may crop the facial image, etc. to generate a left eye cropped image and a right eye cropped image. In performing the conjunctival hyperemia prediction method, the server 20 may use the first cropping (eyeball-exposed-to-outside cropping) method among the three cropping methods described above. Since the first cropping method has already been described in detail, a detailed description thereof will be omitted here.

Resizing Processing and Lateral Inversion Processing

The server 20 may resize the size of the left eye cropped image and of the right eye cropped image to a predetermined size.

In the meantime, the server 20 may laterally invert either the left eye cropped image or the right eye cropped image as described above. The server 20 does not laterally invert the other among the left eye cropped image and the right eye cropped image. Herein, it is determined that the criterion for determining which one of the left eye image and the right eye image is subjected to lateral inversion is the same as the criterion applied when the first prediction model is trained. That is, in training the first prediction model, when the left eye image is inverted and the right eye image is not inverted, the server 20 inverts the left eye image and does not invert the right eye image, similarly.

As described above, in realizing the first prediction model, when the first prediction model is dualized to the first left eye prediction model and the first right eye prediction model, the server 20 may not perform lateral inversion processing.

In the meantime, it has been described that when preprocessing is performed, cropping processing, resizing processing, and lateral inversion processing are performed, but the sequence of these types of preprocessing may be changed within a range capable of achieving the purpose of the conjunctival hyperemia prediction method disclosed in the present application.

Input of Preprocessed Image

The server 20 may input the preprocessed image to the first prediction model in step S120.

When the first prediction model is not dualized and is realized as one model, the server 20 inputs the right eye preprocessed image and the laterally inverted left eye preprocessed image to the first prediction model in order.

In realizing the first prediction model, when the first prediction model is dualized to the first left eye prediction model and the first right eye prediction model, the server 20 inputs the left eye preprocessed image to the first left eye prediction model and inputs the right eye preprocessed image to the first right eye prediction model. Alternatively, the server 20 may input the left eye preprocessed image and the laterally inverted right eye preprocessed image to the first left eye prediction model, and may input the right eye preprocessed image and the laterally inverted left eye preprocessed image to the first right eye prediction model.

In realizing the first prediction model, when the first prediction model is not dualized and is realized as one model and, simultaneously, is trained to be capable of determining whether there is conjunctival hyperemia without distinguishing between a left eye image and a right eye image, the server 20 may input the left eye preprocessed image and the right eye preprocessed image to the first prediction model without lateral inversion. Alternatively, the server 20 may input the left eye preprocessed image, the laterally inverted left eye preprocessed image, the right eye preprocessed image, and the laterally inverted right eye preprocessed image to the first prediction model.

Conjunctival Hyperemia Prediction Result

The server 20 may output a result value output from the first prediction model in step S130. The result value may be a probability value that is predicted with respect to conjunctival hyperemia captured in an image. However, as described above, since the first prediction model is trained to output a conjunctival edema prediction value, a lacrimal edema prediction value, an eyelid redness prediction value, and an eyelid edema prediction value in addition to a conjunctival hyperemia prediction value, the server 20 may obtain all the result values related to the five types of evaluated values from the first prediction model. Herein, the server 20 selects only the conjunctival hyperemia prediction value among the conjunctival hyperemia prediction value, the conjunctival edema prediction value, the lacrimal edema prediction value, the eyelid redness prediction value, and the eyelid edema prediction value. Furthermore, on the basis of a relationship between the selected conjunctival hyperemia prediction value and a threshold and prediction results for the left eye and the right eye, a result for whether there is conjunctival hyperemia is finally output.

When the server 20 inputs the left eye preprocessed image to the first left eye prediction model, inputs the laterally inverted left eye preprocessed image to the first right eye prediction model, inputs the right eye preprocessed image to the first right eye prediction model, and inputs the laterally inverted right eye preprocessed image to the first left eye prediction model, the server 20 may obtain a prediction result for the left eye considering both a result obtained by inputting the left eye preprocessed image to the first left eye prediction model and a result obtained by inputting the laterally inverted left eye preprocessed image to the first right eye prediction model. Herein, the server 20 may obtain a prediction result for the right eye considering both a result obtained by inputting the right eye preprocessed image to the first right eye prediction model and a result obtained by inputting the laterally inverted right eye preprocessed image to the first left eye prediction model.

For example, the server 20 may obtain a prediction result for the left eye on the basis of whether an average value of the result obtained by inputting the left eye preprocessed image to the first left eye prediction model and the result obtained by inputting the laterally inverted left eye preprocessed image to the first right eye prediction model is equal to or greater than the threshold value.

As another example, when a value of either the result obtained by inputting the left eye preprocessed image to the first left eye prediction model or the result obtained by inputting the laterally inverted left eye preprocessed image to the first right eye prediction model is equal to or greater than the above-described threshold value, the server 20 may predict that the conjunctiva of the left eye is hyperemic.

As still another example, when both the result obtained by inputting the left eye preprocessed image to the first left eye prediction model and the result obtained by inputting the laterally inverted left eye preprocessed image to the first right eye prediction model are equal to or greater than the above-described threshold value, the server 20 may predict that the conjunctiva of the left eye is hyperemic.

When the server 20 inputs the left eye preprocessed image, the laterally inverted left eye preprocessed image, the right eye preprocessed image, and the laterally inverted right eye preprocessed image to the first prediction model that is not dualized, the server 20 may obtain a prediction result for the left eye considering both a result obtained by inputting the left eye preprocessed image to the first prediction model and a result obtained by inputting the laterally inverted left eye preprocessed image to the first prediction model. Herein, the server 20 may obtain a prediction result for the right eye considering both a result obtained by inputting the right eye preprocessed image to the first prediction model and a result obtained by inputting the laterally inverted right eye preprocessed image to the first prediction model.

For example, the server 20 may obtain a prediction result for the left eye on the basis of whether an average value of the result obtained by inputting the left eye preprocessed image to the first prediction model and the result obtained by inputting the laterally inverted left eye preprocessed image to the first prediction model is equal to or greater than the threshold value.

As another example, when a value of either the result obtained by inputting the left eye preprocessed image to the first prediction model or the result obtained by inputting the laterally inverted left eye preprocessed image to the first prediction model is equal to or greater than the above-described threshold value, the server 20 may predict that the conjunctiva of the left eye is hyperemic.

As still another example, when both the result obtained by inputting the left eye preprocessed image to the first prediction model and the result obtained by inputting the laterally inverted left eye preprocessed image to the first prediction model are equal to or greater than the above-described threshold value, the server 20 may predict that the conjunctiva of the left eye is hyperemic.

The above-described method may be similarly applied in determining whether there is conjunctival hyperemia of the right eye.

6. Conjunctival Edema Prediction Method

The conjunctival edema prediction method described in the present application may be performed by the server 20.

Figure 20:
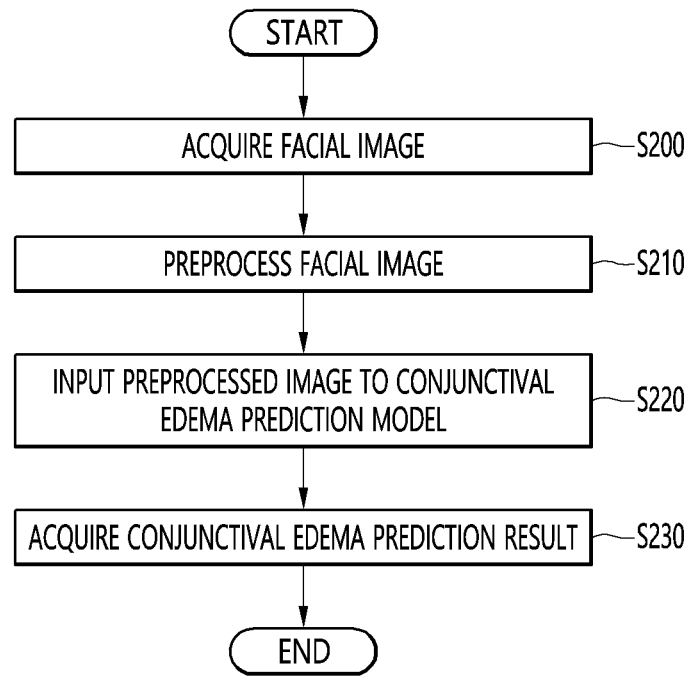
FIG. 20 is a flowchart illustrating a conjunctival edema prediction method.

FIG. 20 is a flowchart illustrating a conjunctival edema prediction method.

Referring to FIG. 20, the server 20 acquires a facial image in step S200, preprocesses the acquired facial image in step S210, inputs the preprocessed image to the above-describe second prediction model (conjunctival edema prediction model) in step S220, and acquires an output value of the second prediction model in step S230.

The conjunctival edema prediction method is the same as or very similar to the conjunctival hyperemia prediction method except that the second prediction model is used instead of the first prediction model and a finally acquired result value is a predicted value for whether there is conjunctival edema (among the five types of result values, only the result value for conjunctival edema is selected), so a detailed description of the conjunctival edema prediction method will be omitted.

7. Lacrimal Edema Prediction Method

The lacrimal edema prediction method described in the present application may be performed by the server 20.

Figure 21:
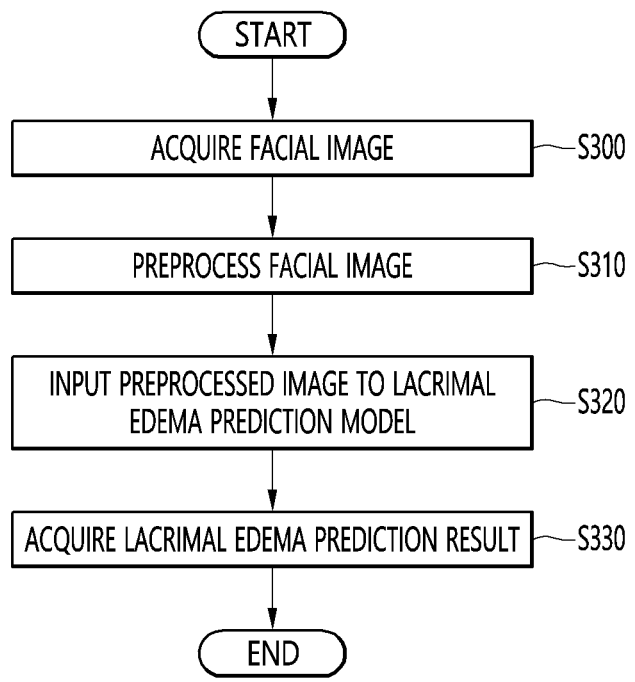
FIG. 21 is a flowchart illustrating a lacrimal edema prediction method.

FIG. 21 is a flowchart illustrating a lacrimal edema prediction method.

Referring to FIG. 21, the server 20 acquires a facial image in step S300, preprocesses the acquired facial image in step S310, inputs the preprocessed image to the above-described third prediction model (lacrimal edema prediction model) in step S320, and acquires an output value of the third prediction model in step S330.

The lacrimal edema prediction method is the same as or very similar to the conjunctival hyperemia prediction method except that the third prediction model is used instead of the first prediction model, the third cropped image is used instead of the first cropped image, and a finally acquired result value is a predicted value for whether there is lacrimal edema (among the five types of result values, only the result value for lacrimal edema is selected), so a detailed description of the conjunctival edema prediction method will be omitted.

8. Eyelid Redness Prediction Method

The eyelid redness prediction method described in the present application may be performed by the server 20.

Figure 22:
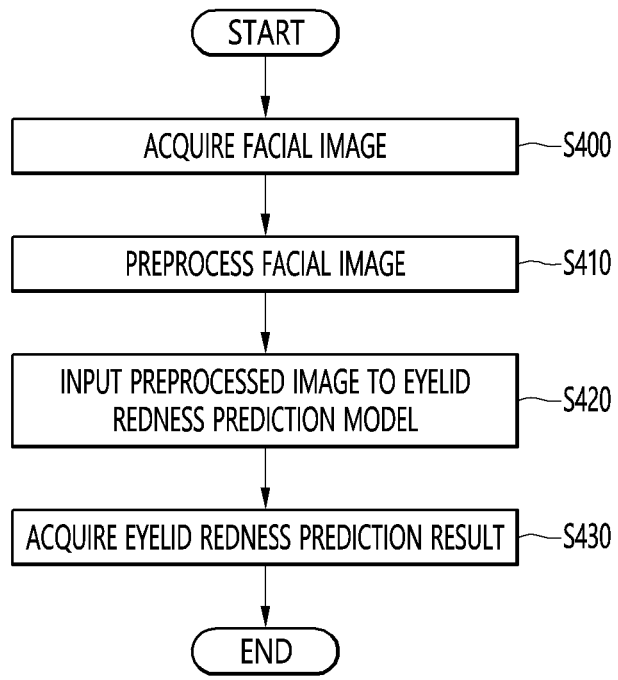
FIG. 22 is a flowchart illustrating an eyelid redness prediction method.

FIG. 22 is a flowchart illustrating an eyelid redness prediction method.

Referring to FIG. 22, the server 20 acquires a facial image in step S400, preprocesses the acquired facial image in step S410, inputs the preprocessed image to the above-described fourth prediction model (eyelid redness prediction model) in step S420, and acquires an output value of the fourth prediction model in step S430.

The eyelid redness prediction method is the same as or very similar to the conjunctival hyperemia prediction method except that the fourth prediction model is used instead of the first prediction model, the second cropped image is used instead of the first cropped image, and a finally acquired result value is a predicted value for whether there is eyelid redness (among the five types of result values, only the result value for eyelid redness is selected), so a detailed description of the eyelid redness prediction method will be omitted.

9. Eyelid Edema Prediction Method

The eyelid edema prediction method described in the present application may be performed by the server 20.

Figure 23:
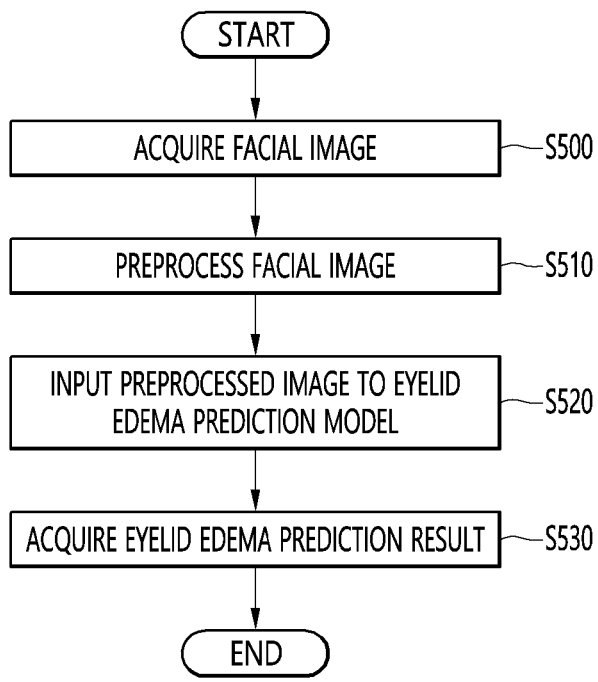
FIG. 23 is a flowchart illustrating an eyelid edema prediction method.

FIG. 23 is a flowchart illustrating an eyelid edema prediction method.

Referring to FIG. 23, the server 20 acquires a facial image in step S500, preprocesses the acquired facial image in step S510, inputs the preprocessed image to the above-described fifth prediction model (eyelid edema prediction model) in step S520, and acquires an output value of the fifth prediction model in step S530.

The eyelid edema prediction method is the same as or very similar to the conjunctival hyperemia prediction method except that the fifth prediction model is used instead of the first prediction model, the second cropped image is used instead of the first cropped image, and a finally acquired result value is a predicted value for whether there is eyelid edema (among the five types of result values, only the result value for eyelid edema is selected), so a detailed description of the eyelid redness prediction method will be omitted.

10. Method of Predicting Clinical Activity Score for Thyroid Eye Disease

Hereinafter, described will be a method, which is described in the present application, of predicting a clinical activity score for thyroid eye disease.

Figure 24:
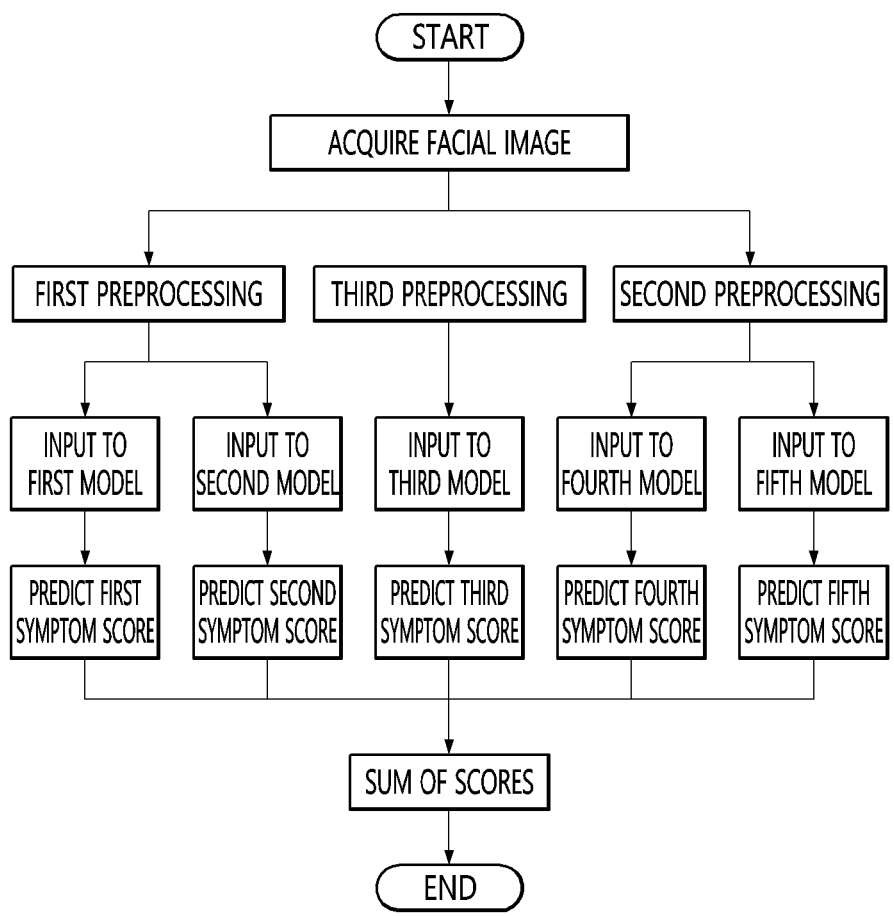
FIG. 24 is a diagram illustrating a method of predicting a clinical activity score for thyroid eye disease.

FIG. 24 is a diagram illustrating a method of predicting a clinical activity score for thyroid eye disease.

The server 20 may acquire a facial image.

The server 20 performs three different types of preprocessing on one facial image. First preprocessing (hereinafter, first preprocessing) includes first cropping (eyeball-exposed-to-outside cropping), resizing, and lateral inversion. Second preprocessing (hereinafter, second preprocessing) includes second cropping (eyelid-included cropping), resizing, and lateral inversion. Third preprocessing (hereinafter, third preprocessing) includes third cropping (lacrimal caruncle-included cropping), resizing, and lateral inversion. However, as described above, whether to perform lateral inversion may be omitted in all the preprocessing methods, and whether to perform lateral inversion may be determined according to which method is used for the training method of each of the prediction models.

The server 20 acquires a first preprocessed image by performing first preprocessing on the acquired facial image, and the first preprocessed image includes a first left eye preprocessed image and a first right eye preprocessed image. Herein, either the first left eye preprocessed image or the first right eye preprocessed image may be an image on which lateral inversion is processed. Alternatively, a first left eye preprocessed image, a first left eye preprocessed image subjected to lateral inversion, a first right eye preprocessed image, and a first right eye preprocessed image subjected to lateral inversion may be generated. Furthermore, as already described in detail, since the first preprocessed image is an image obtained using first cropping, the number of pixels corresponding to the eyelids within the first preprocessed image is minimized and the pixels corresponding to the eyeballs exposed to the outside are included.

In addition, the server 20 acquires a second preprocessed image by performing second preprocessing on the acquired facial image, and the second preprocessed image includes a second left eye preprocessed image and a second right eye preprocessed image. Herein, either the second left eye preprocessed image or the second right eye preprocessed image may be an image on which lateral inversion is processed. Alternatively, a second left eye preprocessed image, a second left eye preprocessed image subjected to lateral inversion, a second right eye preprocessed image, and a second right eye preprocessed image subjected to lateral inversion may be generated. Furthermore, as already described in detail, since the second preprocessed image is an image obtained by using second cropping, the second preprocessed image includes sufficient pixels corresponding to eyelids.

In addition, the server 20 acquires a third preprocessed image by performing third preprocessing on the acquired facial images, and the third preprocessed image includes a third left eye preprocessed image and a third right eye preprocessed image. Herein, either the third left eye preprocessed image or the third right eye preprocessed image may be an image on which lateral inversion is processed. Alternatively, a third left eye preprocessed image, a third left eye preprocessed image subjected to lateral inversion, a third right eye preprocessed image, and a third right eye preprocessed image subjected to lateral inversion may be generated. Furthermore, as already described in detail, since the third preprocessed image is an image obtained by using third cropping, the third preprocessed image includes sufficient pixels corresponding to lacrimal caruncles.

The server 20 inputs the first preprocessed image (the first left eye preprocessed image and the first right eye preprocessed image) to the first prediction model in order. The server 20 obtains a result value (probability value) of the first prediction model for the first left eye preprocessed image, and determines, on the basis of the result value, whether there is conjunctival hyperemia of the left eye. In addition, the server 20 obtains a result value (probability value) of the first prediction model for the first right eye preprocessed image, and determines, on the basis of the result value, whether there is conjunctival hyperemia of the right eye.

The server 20 synthesizes a determination result for the left eye and a determination result for the right eye, and finally determines whether there is conjunctival hyperemia of both eyes. For example, when determining that there is conjunctival hyperemia of either the left eye or the right eye or both, the server 20 finally determines that there is conjunctival hyperemia.

Next, the server 20 inputs the first preprocessed image (the first left eye preprocessed image and the first right eye preprocessed image) to the second prediction model in order. The server 20 obtains a result value (probability value) of the second prediction model for the first left eye preprocessed image, and determines, on the basis of the result value, whether there is conjunctival edema of the left eye. In addition, the server 20 obtains a result value (probability value) of the second prediction model for the first right eye preprocessed image, and determines, on the basis of the result value, whether there is conjunctival edema of the right eye.

The server 20 synthesizes a determination result for the left eye and a determination result for the right eye, and finally determines whether there is conjunctival edema of both eyes. For example, when determining that there is conjunctival edema of either the left eye or the right eye or both, the server 20 finally determines that there is conjunctival edema.

Next, the server 20 inputs the third preprocessed image (the third left eye preprocessed image and the third right eye preprocessed image) to the third prediction model in order. The server 20 obtains a result value (probability value) of the third prediction model for the third left eye preprocessed image, and determines, on the basis of the result value, whether there is lacrimal edema of the left eye. In addition, the server 20 obtains a result value (probability value) of the third prediction model for the third right eye preprocessed image, and determines, on the basis of the result value, whether there is lacrimal edema of the right eye.

The server 20 synthesizes a determination result for the left eye and a determination result for the right eye, and finally determines whether there is lacrimal edema of both eyes. For example, when determining that there is lacrimal edema of either the left eye or the right eye or both, the server 20 finally determines that there is lacrimal edema.

The server 20 inputs the second preprocessed image (the second left eye preprocessed image and the second right eye preprocessed image) to the fourth prediction model in order. The server 20 obtains a result value (probability value) of the fourth prediction model for the second left eye preprocessed image, and determines, on the basis of the result value, whether there is eyelid redness of the left eye. In addition, the server 20 obtains a result value (probability value) of the fourth prediction model for the second right eye preprocessed image, and determines, on the basis of the result value, whether there is eyelid redness of the right eye.

The server 20 synthesizes a determination result for the left eye and a determination result for the right eye, and finally determines whether there is eyelid redness of both eyes. For example, when determining that there is eyelid redness of either the left eye or the right eye or both, the server 20 finally determines that there is eyelid redness.

The server 20 inputs the second preprocessed image (the second left eye preprocessed image and the second right eye preprocessed image) to the fifth prediction model in order. The server 20 obtains a result value (probability value) of the fifth prediction model for the second left eye preprocessed image, and determines, on the basis of the result value, whether there is eyelid edema of the left eye. In addition, the server obtains a result value (probability value) of the fifth prediction model for the second right eye preprocessed image, and determines, on the basis of the result value, whether there is eyelid edema of the right eye.

The server 20 synthesizes a determination result for the left eye and a determination result for the right eye, and finally determines whether there is eyelid edema of both eyes. For example, when determining that there is eyelid edema of either the left eye or the right eye or both, the server 20 finally determines that there is eyelid edema.

When it is determined that there is a symptom through a prediction model, the server 20 may give a predetermined score (for example, a score of 1) for the symptom. The server may give scores for five respective symptoms according to determination results for the five prediction models, and may also obtain a value obtained by adding all the scores.

In the meantime, the server 20 may transmit the results determined by the prediction models and/or information on the scores given on the basis of the results to a user terminal 10.

In addition, the user terminal 10 or the server 20 may obtain the user's response to the two items including spontaneous retrobulbar pain and pain on an attempted upward or downward gaze, and on the basis of the obtained user's response, the user terminal 10 or the server 20 may give a predetermined score (for example, a score of 1) for each of the items. For example, when the user provides an input that the user has spontaneous retrobulbar pain, a score of 1 may be given. In addition, the user provides an input that the user has pain on an attempted upward or downward gaze, a score of 1 may be given.

The server 20 or the user terminal 10 may recommend that the user visit the hospital and have a detailed medical examination, considering the scores based on the results determined by the prediction models and the scores determined with respect to the spontaneous retrobulbar pain and the pain on an attempted upward or downward gaze.

It has been described that the above-described method, which is described in the present application, of predicting a clinical activity score for thyroid eye disease is performed by the server 20. However, the above-described method may be performed by a user terminal 10. Alternatively, preprocessing of the above-described methods may be performed by the user terminal 10, and determination for each of the symptoms may be performed by the server. That is, the above-described steps may be appropriately distributed to the user terminal 10 and the server 20 and performed.

11. Experimental Example #1

(1) Preparation of Facial Images 1,020 facial images were prepared. Each of the facial images was an image including both a left eye and a right eye, and was an image obtained according to a predetermined photographing structure.

(2) Securing Labeling Information of Facial Images

For each of the 1,020 facial images, information on conjunctival hyperemia, conjunctival edema, lacrimal edema, eyelid redness, and eyelid edema for the left eye, and information on conjunctival hyperemia, conjunctival edema, lacrimal edema, eyelid redness, and eyelid edema for the right eye were secured, and the data were used as labeling data.

Among 1,020 data sets, 714 data sets were used as a training data set (training set), 102 data sets were used as a validation sets, and 204 data sets were used as a test set.

Furthermore, dividing the 1,020 data sets into a training data set, a validation set, and a test set was randomly performed 30 times, and a first training data set group to a 30th training data set group were created accordingly.

(3) Securing Preprocessed Images of Facial Images

For each of the 1,020 facial images, first cropping processing (eyeball-exposed-to-outside cropping) was performed on each of the left eye and the right eye in the above-described manner to secure a first left eye preprocessed image and a first right eye preprocessed image. Herein, a laterally inverted image was used as the first right eye preprocessed image, and a non-laterally inverted image was used as the first left eye preprocessed image.

For each of the 1,020 facial images, second cropping processing (eyelid-included cropping) was performed on each of the left eye and the right eye in the above-described manner to secure a second left eye preprocessed image and a second right eye preprocessed image. Herein, a laterally inverted image was used as the second right eye preprocessed image, and a non-laterally inverted image was used as the second left eye preprocessed image.

For each of the 1,020 facial images, third cropping processing (lacrimal caruncle-included cropping) was performed on each of the left eye and the right eye in the above-described manner to secure a third left eye preprocessed image and a third right eye preprocessed image. Herein, a laterally inverted image was used as the third right eye preprocessed image, and a non-laterally inverted image was used as the third left eye preprocessed image.

The above-described image processing was performed on all the 30 data set groups.

(4) Training of First to Fifth Prediction Models According to Experimental Example #1

Using the secured preprocessed images and the secured pieces of labeling information, the prediction models were trained. As the prediction models, the models using the above-described ViT as the backbone architecture were used, and finally, five output nodes were designed. As the training method, the method in which all the five types of evaluated values were used in training of each of the models was used as described above.

In the meantime, as the prediction models, the models using the above-described ViT as the backbone architecture were used, and each of the prediction models was trained with unification as one model without dividing into a left eye prediction model and a right eye prediction model.

(5) Acquisition of Prediction Result for Each Symptom by Using Prediction Models Prediction results were acquired using the test data sets for the trained first to fifth prediction models. Herein, a laterally inverted preprocessed image was used as a right eye image, and a non-laterally inverted preprocessed image was as a left eye image.

(6) Accuracy, Sensitivity, Specificity, Positive Predictive Value (PPV), and Negative Predictive Value (NPV) of Prediction Models According to Experimental Example #1

The values shown in [Table 1] are average values of accuracy, sensitivity, specificity, PPV, and NPV measured for the first to fifth prediction models that were trained for each of the 30 data set groups according to the above-described experimental example #1.

TABLE 1

| | Accuracy (%) | Sensitivity (%) | Specificity (%) | PPV (%) | NPV (%) |
|---|---|---|---|---|---|
| Conjunctival hyperemia (first prediction model) | 71.80 | 49.71 | 83.43 | 61.61 | 75.62 |
| Conjunctival edema (second prediction model) | 93.90 | 15.72 | 99.78 | 91.00 | 89.32 |
| Lacrimal edema (third prediction model) | 92.15 | 21.77 | 98.69 | 67.23 | 91.09 |
| Eyelid redness (fourth prediction model) | 80.90 | 57.68 | 89.93 | 69.74 | 84.08 |
| Eyelid edema (fifth prediction model) | 64.80 | 74.81 | 45.80 | 72.57 | 48.68 |

12. Comparative Example #1

(1) Preparation of Facial Images

The facial images used in experimental example #1 were used as they were.

(2) Securing Labeling Information of Facial Images

The pieces of labeling information of the facial images used in experimental example #1 were used as they were. However, in generating data sets, rather than a method of generating data sets by matching all the five types of evaluated values to each of the images, a method of generating data sets by matching different evaluated values for each of the models was used.

(3) Securing Eyebrow-Included Preprocessed Images for Facial Images

The preprocessed images used in experimental example #1 were used as they were.

The above-described image processing was performed on all the 30 data set groups.

(4) Training of First to Fifth Prediction Models According to Comparative Example #2

Using the secured preprocessed images and the secured pieces of labeling information, the prediction models were trained. As the prediction models, the models using the above-described ViT as the backbone architecture were used, and finally, one output node was designed, unlike experimental example #1.

Herein, the first prediction model was trained using evaluated values for conjunctival hyperemia, the second prediction model was trained using evaluated values for conjunctival edema, the third prediction model was trained using evaluated values for lacrimal edema, the fourth prediction model was trained using evaluated values for eyelid redness, and the fifth prediction model was trained using evaluated values for eyelid edema.

(5) Acquisition of Prediction Result for Each Symptom by Using Prediction Models Prediction results were acquired using the test data sets for the trained first to fifth prediction models. Herein, a laterally inverted preprocessed image was used as a right eye image, and a non-laterally inverted preprocessed image was as a left eye image.

(6) Accuracy, Sensitivity, Specificity, Positive Predictive Value (PPV), and Negative Predictive Value (NPV) of Prediction Models According to Comparative Example #2

The values shown in [Table 2] are average values of accuracy, sensitivity, specificity, PPV, and NPV measured for the first to fifth prediction models that were trained for each of the 30 data set groups according to the above-described experimental example #2.

TABLE 2

| | Accuracy (%) | Sensitivity (%) | Specificity (%) | PPV (%) | NPV (%) |
|---|---|---|---|---|---|
| Conjunctival hyperemia (first prediction model) | 62.50 | 26.23 | 81.60 | 46.96 | 64.04 |
| Conjunctival edema (second prediction model) | 89.40 | 1.43 | 96.02 | 1.03 | 97.11 |
| Lacrimal edema (third prediction model) | 90.90 | 16.47 | 97.81 | 59.84 | 85.53 |
| Eyelid redness (fourth prediction model) | 70.00 | 33.93 | 84.03 | 50.62 | 72.50 |
| Eyelid edema (fifth prediction model) | 59.55 | 72.90 | 34.20 | 67.90 | 39.79 |

13. Experimental Example #2

(1) Preparation of Facial Images

The facial images used in experimental example #1 were used as they were.

(2) Securing Labeling Information of Facial Images

The pieces of labeling information of the facial images used in experimental example #1 were used as they were.

(3) Securing Eyebrow-Included Preprocessed Images for Facial Images

For each of the 1,020 facial images, second cropping processing (eyelid-included cropping) was performed on each of the left eye and the right eye in the above-described manner to secure a second left eye preprocessed image and a second right eye preprocessed image. Herein, a laterally inverted image was used as the first right eye preprocessed image, and a non-laterally inverted image was used as the first left eye preprocessed image.

(4) Training of Fourth and Fifth Prediction Models According to Experimental Example #2

Using the secured preprocessed images and the secured pieces of labeling information, the prediction models were trained. As the prediction models, the models using the above-described ViT as the backbone architecture were used, and finally, five output nodes were designed. As the training method, the method in which all the five types of evaluated values were used in training of each of the models was used as described above.

(5) Accuracy, Sensitivity, Specificity, Positive Predictive Value (PPV), and Negative Predictive Value (NPV) of Eyelid Redness Prediction Model and Eyelid Edema Prediction Model According to Experimental Example #2

The values shown in [Table 3] are average values of accuracy, sensitivity, specificity, PPV, and NPV measured for the fourth and fifth prediction models that were trained for each of the 30 data set groups according to the above-described experimental example #2.

TABLE 3

|  | Accuracy (%) | Sensitivity (%) | Specificity (%) | PPV (%) | NPV (%) |
|---|---|---|---|---|---|
| Eyelid redness (fourth prediction model) | 76.13 | 70.65 | 79.08 | 64.63 | 83.86 |
| Eyelid edema (fifth prediction model) | 81.29 | 86.38 | 53.52 | 91.16 | 43.59 |

14. Experimental Example #3

(1) Preparation of Facial Images

The facial images used in experimental example #1 were used as they were.

(2) Securing Labeling Information of Facial Images

The pieces of labeling information of the facial images used in experimental example #1 were used as they were.

(3) Securing Eyebrow-Included Preprocessed Images for Facial Images

For each of the 1,020 facial images, second cropping processing (eyelid-included cropping) was performed on each of the left eye and the right eye in the above-described manner. However, unlike experimental example #2, a second cropped region was determined such that the central position of the second cropped region was placed higher than the central position of the reference quadrangle. Accordingly, a second cropped image included an eyebrow. Herein, lateral inversion processing was not performed in securing a second left eye preprocessed image and a second right eye preprocessed image.

(4) Training of Fourth and Fifth Prediction Models According to Experimental Example #3

Using the secured preprocessed images and the secured pieces of labeling information, the prediction models were trained. As the prediction models, the models using the above-described ViT as the backbone architecture were used, and finally, five output nodes were designed. As the training method, the method in which all the five types of evaluated values were used in training of each of the models was used as described above.

(5) Accuracy, Sensitivity, Specificity, Positive Predictive Value (PPV), and Negative Predictive Value (NPV) of Eyelid Redness Prediction Model and Eyelid Edema Prediction Model According to Experimental Example #3

The values shown in [Table 4] are average values of accuracy, sensitivity, specificity, PPV, and NPV measured for the fourth and fifth prediction models that were trained for each of the 30 data set groups according to the above-described experimental example #3.

TABLE 4

|  | Accuracy (%) | Sensitivity (%) | Specificity (%) | PPV (%) | NPV (%) |
|---|---|---|---|---|---|
| Eyelid redness (fourth prediction model) | 75.41 | 71.14 | 77.64 | 63.96 | 84.09 |
| Eyelid edema (fifth prediction model) | 79.80 | 89.27 | 57.42 | 91.51 | 41.38 |

1: System
10: User terminal
20: Server

The invention claimed is:

1. A computer-implemented method for treatment for thyroid eye disease, comprising:
training a conjunctival hyperemia prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, and the training image includes at least a part of eyes,
acquiring a first image including at least one eye of a subject and an outer region of an outline of the at least one eye,
cropping, laterally inverting, or resizing the first image based on the outer region of the outline of the at least one eye to obtain a transformed image,
inputting the transformed image to the trained conjunctival hyperemia prediction model executing on a processor to obtain a first predicted value for a conjunctival hyperemia, a first predicted value for the conjunctival edema, a first predicted value for an eyelid redness, a first predicted value for an eyelid edema, and a first predicted value for a lacrimal edema,
selecting the first predicted value for the conjunctival hyperemia among the five predicted values based on a predetermined setting, and
generating a score for the conjunctival hyperemia based on the selected first predicted value for a conjunctival hyperemia, that is used to recommend to the subject to have a medical examination based on the score.

2. The computer-implemented method of claim 1, wherein the first image is generated in relation to any one eye among both eyes, and
wherein the generated predicted values are predicted values for the one eye.

3. The computer-implemented method of claim 2, further comprising:
acquiring a second image comprising other eye and an outer region of an outline of the other eye of the subject,
outputting, by the conjunctival hyperemia prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival hyperemia among the five predicted values based on a predetermined setting, and wherein the generating a score for the conjunctival hyperemia is generating a score for the conjunctival hyperemia considering the selected first predicted value for the conjunctival hyperemia and the selected second predicted value for the conjunctival hyperemia.

4. The computer-implemented method of claim 3, wherein the generating the score for the conjunctival hyperemia comprises, assigning a predetermined value to the score:

in response to determining that the first predicted value for the conjunctival hyperemia being greater than a threshold value, in response to determining that the second predicted value for the conjunctival hyperemia being greater than the threshold value, or in response to determining that the first and second predicted values for the conjunctival hyperemia being greater than the threshold value.

5. A computer-implemented method for treatment for thyroid eye disease, comprising:

training a conjunctival edema prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for a lacrimal edema, wherein the training image is annotated with the evaluated values according to a diagnosis of the training image, and the training image includes at least a part of eyes, acquiring a first image including at least one eye of a subject and an outer region of an outline of the at least one eye, cropping, laterally inverting, or resizing the first image based on the outer region of the outline of the at least one eye to obtain a transformed image, inputting the transformed image to the trained conjunctival edema prediction model executing on a processor to obtain a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the conjunctival edema among the five predicted values based on a predetermined setting, and generating a score for the conjunctival edema based on the selected first predicted value for a conjunctival edema, that is used to recommend to the subject to have a medical examination based on the score.

6. The computer-implemented method of claim 5, wherein the first image is generated in relation to any one eye among both eyes, and wherein the generated predicted values are predicted values for the one eye.

7. The computer-implemented method of claim 6, further comprising:

acquiring a second image comprising other eye and an outer region of an outline of the other eye of the subject, outputting, by the conjunctival edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the conjunctival edema among the five predicted values based on a predetermined setting, and wherein the generating a score for the conjunctival edema is generating a score for the conjunctival edema considering the selected first predicted value for the conjunctival edema and the selected second predicted value for the conjunctival edema.

8. The computer-implemented method of claim 7, wherein the generating the score for the conjunctival edema comprises, assigning a predetermined value to the score:

in response to determining that the first predicted value for the conjunctival edema being greater than a threshold value, in response to determining that the second predicted value for the conjunctival edema being greater than the threshold value, or in response to determining that the first and second predicted values for the conjunctival edema being greater than the threshold value.

9. A computer-implemented method for treatment for thyroid eye disease, comprising:

training a lacrimal edema prediction model using a training set, wherein the training set comprises a training image, an evaluated value for a conjunctival hyperemia, an evaluated value for a conjunctival edema, an evaluated value for an eyelid redness, an evaluated value for an eyelid edema, and an evaluated value for the lacrimal edema, wherein the training image is annotated with the evaluated values according to a diagnosis of the training image, and the training image includes at least a part of eyes, acquiring a first image including at least one eye of a subject and an outer region of an outline of the at least one eye, cropping, laterally inverting, or resizing the first image based on the outer region of the outline of the at least one eye to obtain a transformed image, inputting the transformed image to the trained lacrimal edema prediction model executing on a processor to obtain a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the lacrimal edema among the five predicted values based on a predetermined setting, and generating a score for the lacrimal edema based on the selected first predicted value for a lacrimal edema, that is used to recommend to the subject to have a medical examination based on the score.

10. The computer-implemented method of claim 9, wherein the first image is generated in relation to any one eye among both eyes, and wherein the generated predicted values are predicted values for the one eye.

11. The computer-implemented method of claim 10, further comprising:

acquiring a second image comprising other eye and an outer region of an outline of the other eye of the subject, outputting, by the lacrimal edema prediction model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the lacrimal edema among the five predicted values based on a predetermined setting, and wherein the generating a score for the lacrimal edema is generating a score for the lacrimal edema considering the selected first predicted value for the lacrimal edema and the selected second predicted value for the lacrimal edema.

12. The computer-implemented method of claim 11, wherein the generating the score for the lacrimal edema comprises, assigning a predetermined value to the score:

in response to determining that the first predicted value for the lacrimal edema being greater than a threshold value, in response to determining that the second predicted value for the lacrimal edema being greater than the threshold value, or in response to determining that the first and second predicted values for the lacrimal edema being greater than the threshold value.

13. A computer-implemented method for treatment for thyroid eye disease, comprising:

training an eyelid redness prediction model using a training set, wherein the training set comprises a training image, an evaluated value for a conjunctival hyperemia, an evaluated value for a conjunctival edema, an evaluated value for the eyelid redness, an evaluated value for an eyelid edema, and an evaluated value for a lacrimal edema, wherein the training image is annotated with the evaluated values according to a diagnosis of the training image, and the training image includes at least a part of eyes, acquiring a first image including at least one eye of a subject and an outer region of an outline of the at least one eye, cropping, laterally inverting, or resizing the first image based on the outer region of the outline of the at least one eye to obtain a transformed image, inputting the transformed image to the trained eyelid redness prediction model executing on a processor to obtain a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid redness among the five predicted values based on a predetermined setting, and generating a score for the eyelid redness based on the selected first predicted value for the eyelid redness, that is used to recommend to the subject to have a medical examination based on the score.

14. The computer-implemented method of claim 13, wherein the first image is generated in relation to any one eye among both eyes, and wherein the generated predicted values are predicted values for the one eye.

15. The computer-implemented method of claim 14, further comprising:

acquiring a second image comprising other eye and an outer region of an outline of the other eye of the subject, outputting, by the eyelid redness model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid redness among the five predicted values based on a predetermined setting, and wherein the generating a score for the eyelid redness is generating a score for the eyelid redness considering the selected first predicted value for the eyelid redness and the selected second predicted value for the eyelid redness.

16. The computer-implemented method of claim 15, wherein the generating the score for the eyelid redness comprises, assigning a predetermined value to the score:

in response to determining that the first predicted value for the eyelid redness being greater than a threshold value, in response to determining that the second predicted value for the eyelid redness being greater than the threshold value, or in response to determining that the first and second predicted values for the eyelid redness being greater than the threshold value.

17. The computer-implemented method of claim 13, further comprising:

training an eyelid edema prediction model using a training set, wherein the training set comprises a training image, an evaluated value for a conjunctival hyperemia, an evaluated value for the conjunctival edema, an evaluated value for the eyelid redness, an evaluated value for the eyelid edema, and an evaluated value for the lacrimal edema, wherein the training image is annotated with the evaluated values according to a diagnosis of the training image, acquiring a first image include at least one eye of a subject and an outer region of an outline of the at least one eye, outputting, by the eyelid edema prediction model executing on a processor, a first predicted value for a conjunctival hyperemia, a first predicted value for the conjunctival edema, a first predicted value for an eyelid redness, a first predicted value for an eyelid edema, and a first predicted value for a lacrimal edema, selecting the first predicted value for the eyelid edema among the five predicted values based on a predetermined setting, and generating a score for the eyelid edema based on the selected first predicted value for the eyelid edema.

18. The computer-implemented method of claim 17, wherein the first image is generated in relation to any one eye among both eyes, and wherein the generated predicted values are predicted values for the one eye.

19. The computer-implemented method of claim 18, further comprising:

acquiring a second image comprising other eye and an outer region of an outline of the other eye of the subject, outputting, by the eyelid edema model executing on the processor, a second predicted value for the conjunctival hyperemia, a second predicted value for the conjunctival edema, a second predicted value for the eyelid redness, a second predicted value for the eyelid edema, and a second predicted value for the lacrimal edema, and selecting the second predicted value for the eyelid edema among the five predicted values based on a predetermined setting, and wherein the generating a score for the eyelid edema is generating a score for the eyelid edema considering the selected first predicted value for the eyelid edema and the selected second predicted value for the eyelid edema.

20. The computer-implemented method of claim 19, wherein the generating the score for the eyelid edema comprises, assigning a predetermined value to the score:

in response to determining that the first predicted value for the eyelid edema being greater than a threshold value, in response to determining that the second predicted value for the eyelid edema being greater than the threshold value, or in response to determining that the first and second predicted values for the eyelid edema being greater than the threshold value.

\* \* \* \* \*